(12) United States Patent
Vogt et al.

(10) Patent No.: US 10,517,661 B2
(45) Date of Patent: Dec. 31, 2019

(54) BONE CEMENT APPLICATOR WITH THREE-WAY VALVE FOR PRESSURE RELIEF

(71) Applicant: Heraeus Medical Gmbh, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 293 days.

(21) Appl. No.: 15/656,383

(22) Filed: Jul. 21, 2017

(65) Prior Publication Data
US 2018/0021076 A1    Jan. 25, 2018

(30) Foreign Application Priority Data

Jul. 21, 2016   (DE) .......................... 10 2016 113 468

(51) Int. Cl.
*A61B 17/88* (2006.01)
*A61L 27/16* (2006.01)
(Continued)

(52) U.S. Cl.
CPC ...... *A61B 17/8822* (2013.01); *A61B 17/8816* (2013.01); *A61B 17/8825* (2013.01);
(Continued)

(58) Field of Classification Search
CPC . A61B 17/88; A61B 17/8822; A61B 17/8827; A61B 17/8825; A61B 17/8816; A61B 17/8833; A61L 27/50
See application file for complete search history.

(56) References Cited

U.S. PATENT DOCUMENTS

| 2,446,501 A | 8/1948 | Weber |
| 6,676,663 B2 | 1/2004 | Higueras et al. |
| (Continued) | | |

FOREIGN PATENT DOCUMENTS

| DE | 202005010206 U1 | 9/2005 |
| DE | 102005045227 A1 | 3/2007 |
| (Continued) | | |

OTHER PUBLICATIONS

Kuehn, Klaus-Dieter; "Knochenzemente fuer die Endoprothetik"; Springer-Verlag, 2000, pp. 18-19, Springer-Verlag of BertelmannSpringer publishing group, Berlin, Germany.

*Primary Examiner* — Christopher J Beccia
(74) *Attorney, Agent, or Firm* — Norris McLaughlin, P.A.

(57) ABSTRACT

Bone cement applicators and methods for application of a bone cement dough, the applicators and methods comprise a tubular cartridge with an internal space, a dispensing plunger for expelling the starting components through an opening of the cartridge opposite from the dispensing plunger, wherein the dispensing plunger is mobile in longitudinal direction in the internal space of the cartridge. The applicators and methods further comprise a hose, an application opening, a three-way valve operable from outside and arranged or arrangeable in the hose or on a side of the hose facing the cartridge, and a collecting container arranged on the three-way valve. The three-way valve is designed and arranged or arrangeable in the applicator such that it, being in a first position, provides a fluid connection between the application opening and the opening of the cartridge and closes a feed-through to the collecting container and, being in a second position, provides a fluid connection between the application opening and the collecting container and closes a passage to the opening of the cartridge.

15 Claims, 17 Drawing Sheets

(51) Int. Cl.
  *A61L 27/50* (2006.01)
  *B01F 3/12* (2006.01)
  *B01F 3/14* (2006.01)
  *B01F 5/06* (2006.01)
  *B01F 7/00* (2006.01)
  *B01F 7/16* (2006.01)
  *B01F 13/00* (2006.01)
  *B01F 13/10* (2006.01)
  *B01F 15/02* (2006.01)

(52) U.S. Cl.
  CPC ...... *A61B 17/8827* (2013.01); *A61B 17/8833* (2013.01); *A61L 27/16* (2013.01); *A61L 27/50* (2013.01); *B01F 3/1221* (2013.01); *B01F 3/14* (2013.01); *B01F 5/0614* (2013.01); *B01F 7/007* (2013.01); *B01F 7/161* (2013.01); *B01F 13/002* (2013.01); *B01F 13/1027* (2013.01); *B01F 15/0237* (2013.01); *B01F 15/0293* (2013.01); *A61B 2017/8838* (2013.01)

(56) References Cited

U.S. PATENT DOCUMENTS

| | | |
|---|---|---|
| 6,935,541 B1 | 8/2005 | Campbell et al. |
| 7,008,433 B2 | 3/2006 | Voellmicke et al. |
| 7,112,205 B2 | 9/2006 | Carrison |
| 7,524,103 B2 * | 4/2009 | McGill ............ A61B 17/8805 366/189 |
| 8,038,682 B2 | 10/2011 | McGill et al. |
| 8,308,731 B2 | 11/2012 | Valale |
| 8,348,494 B2 | 1/2013 | Melsheimer et al. |
| 8,544,683 B2 | 10/2013 | Springhorn et al. |
| 9,005,209 B2 | 4/2015 | Click et al. |
| 2004/0074927 A1 | 4/2004 | Lafond |
| 2005/0105384 A1 | 5/2005 | Eder et al. |
| 2007/0162042 A1 | 7/2007 | Dunker et al. |
| 2008/0086143 A1 | 4/2008 | Seaton, Jr. et al. |
| 2008/0188858 A1 | 8/2008 | Luzzi et al. |
| 2008/0319445 A9 * | 12/2008 | McGill ............ A61B 17/8822 606/92 |
| 2009/0105144 A1 | 4/2009 | Vogt et al. |
| 2009/0105366 A1 | 4/2009 | Vogt et al. |
| 2010/0262152 A1 | 10/2010 | Shadduck et al. |
| 2012/0071884 A1 * | 3/2012 | Cooper ............ A61B 17/8827 606/93 |
| 2013/0182528 A1 | 7/2013 | Vogt et al. |
| 2016/0178074 A1 | 6/2016 | Aoki |

FOREIGN PATENT DOCUMENTS

| | | |
|---|---|---|
| DE | 102007052116 A1 | 4/2009 |
| DE | 102007050762 B3 | 5/2009 |
| DE | 102008030312 A1 | 1/2010 |
| DE | 10 2010 046 055 A1 | 3/2012 |
| DE | 10 2011 010 763 A1 | 8/2012 |
| DE | 11 2014 003 555 T5 | 4/2016 |
| EP | 1074231 A1 | 2/2001 |
| EP | 1464292 A1 | 10/2004 |
| EP | 1392450 B1 | 7/2005 |
| EP | 1596736 A1 | 11/2005 |
| EP | 1614403 A1 | 1/2006 |
| FR | 1468507 A | 2/1967 |
| WO | 2005/051212 A1 | 6/2005 |
| WO | 2007/000066 A1 | 1/2007 |
| WO | 2008/038322 A2 | 4/2008 |
| WO | 2008/097855 A2 | 8/2008 |

* cited by examiner

BONE CEMENT APPLICATOR WITH THREE-WAY VALVE FOR PRESSURE RELIEF

This application claims foreign priority benefit under 35 U.S.C. 119 of German Application No. DE 10 2016 113 468.6 filed Jul. 21, 2016.

BRIEF DESCRIPTION OF THE DISCLOSURE

The invention relates to a bone cement applicator for application of a bone cement dough in the region of the spine, which therefore is well-suited, in particular, for vertebroplasty.

The invention also relates to a method for application of a bone cement dough, in particular of a pasty multicomponent polymethylmethacrylate bone cement dough using said bone cement applicator.

The subject matter of the invention is, in particular, a simple, inexpensively produced bone cement applicator for vertebroplasty with pasty multicomponent polymethylmethacrylate bone cements by means of which starting components of the polymethylmethacrylate bone cement dough can be mixed and dispensed with manually operated extrusion devices or by means of which the pre-mixed polymethylmethacrylate bone cement dough itself can be dispensed with manually operated extrusion devices.

Conventional polymethylmethacrylate bone cements (PMMA bone cements) are made from a powdered component and a liquid monomer component (K.-D. Kühn: Knochenzemente für die Endoprothetik: Ein aktueller Vergleich der physikalischen and chemischen Eigenschaften handelsüblicher PMMA-Zemente. Springer-Verlag Berlin Heidelberg New York, 2001). After mixing the cement powder with the liquid monomer component, said polymethylmethacrylate bone cements are applied in their non-cured pasty state in the form of a bone cement dough. If mixing systems are used with powder-liquid cements, the bone cement dough is situated in a cartridge. The bone cement dough is squeezed from said cartridge through the motion of a dispensing plunger. The dispensing plungers usually have a diameter of between 30 mm and 40 mm and thus have a surface area of 7.0 cm$^2$ to 12.5 cm$^2$ on the outside that is engaged by the pestle of the extrusion device during the extrusion process. The motion of the dispensing plunger is effected by manually operated mechanical extrusion devices, which are also called applicators. Said manual extrusion devices usually reach an extrusion force in the range of approximately 1.5 kN to 3.5 N.

Pasty two-component bone cements, such as are known, e.g., from DE 10 2007 050 762 B3, DE 10 2008 030 312 A1, and DE 10 2007 052 116 B4, are a more recent development. In these two-component bone cements, two pasty starting components are stored in two separate cartridges having two separate dispensing plungers. During application, both pastes are pressed from the cartridges into a static mixer through the motion of the dispensing plungers, and are dispensed through a dispensing tube once the mixing took place. If the composition of the pasty starting components is appropriate, an immediately tack-free cement dough that is ready for application is obtained after the two starting components are mixed. Accordingly, there are no waiting times until the cement dough becomes tack-free which were always obligatory with the previous conventional polymethylmethacrylate bone cements. This allows valuable operation theatre time to be saved.

The application of the previous conventional PMMA bone cements, which consist of a liquid monomer component and a separately stored cement powder component as starting components, involves the two starting components being mixed in cementing systems and/or vacuum cementing systems and the cement dough thus formed then being extruded by means of manually operated extrusion devices. These simple mechanical extrusion devices utilise, in particular, clamp rods that are driven by a manually-actuated tilting lever as a pestle for extrusion. The manually driven extrusion devices are time-proven throughout the world for decades and as such are the current prior art. Said extrusion devices are advantageous in that the medical user has a feel for the penetration resistance of the bone cement dough into the bone structures (cancellous bone) by means of the manual force to be expended.

In the case of high viscosity pasty starting components and the use of cartridges, in which the dispensing plungers have a total surface area in the range of 7.0 cm$^2$ to 12.5 cm$^2$ at the external plunger sides, which are engaged by the pestles of the extrusion devices, these devices are operable manually either not at all or only while expending a very large force. This exertion of a large force is unreasonable for medical users in the operation theatre.

From the adhesives and sealant industry, electrically driven extrusion devices are known as well. Said devices can be driven both with rechargeable batteries and batteries or by means of a stationary electrical power supply. Said devices can extrude particularly thick pasty masses since their extrusion force is very large in some cases. However, it is one disadvantage of the use of electrical motors that these motors contain non-ferrous metals and are expensive purchases. Since the operation theatre area needs to be kept sterile, said devices need to be sterilised with much effort or may even need to be replaced. The presence of electrical wiring may impede the mobility of the user in the operation theatre.

Moreover, pneumatic devices have been proposed as well. Said devices require a stationary or mobile compressed air connection (U.S. Pat. No. 2,446,501 A; DE 20 2005 010 206 U1). This necessitates compressed air hoses, which may impede the mobility of the user.

Alternatively, the use of compressed gas cartridges to provide compressed gas is feasible just as well. Devices have been proposed for this purpose, in which the supply of compressed gas is controlled by a valve and, in addition, the flow of the viscous mass is controlled by a second valve (US 2004/0074927 A1; U.S. Pat. No. 6,935,541 B1). In these devices, the gas cartridges are integrated into the devices. These systems, which are connected to compressed air or contain compressed gas cartridges, always necessitate the presence of a compressed gas source in the absence of which the systems cannot be used.

U.S. Pat. No. 8,544,683 B2 discloses a cartridge system that is suitable for admixing a small amount to a main starting component. The cartridge system has, aside from a cartridge, a second smaller cartridge arranged in it, whereby, along with the propulsion of a dispensing plunger in the larger cartridge, a dispensing plunger in the smaller cartridge is also driven by a joint connecting element. However, the system is not suitable for mixing the viscous pasty starting components of PMMA bone cement.

A coaxial cartridge system containing a special plunger system is described in the patent, EP 1 392 450 B1. The cartridge system is used in the construction materials chemical industry for storing and mixing pasty two-component sealant masses.

Patent FR 1 468 507 discloses a cartridge system, in which a tubular storage container is arranged in a cartridge. The storage container is connected to the cartridge in one place on the end of the cartridge. During the forward motion of the dispensing plunger in the direction of the cartridge head, the mass contained in the cartridge is extruded and the mass contained in the tubular container is moved in the direction of the cartridge head by squeezing-out.

In vertebroplasty, the application of bone cement dough is monitored in situ by means of an x-ray procedure. Application devices for vertebroplasty usually have a hose inserted in them through the tip of which the bone cement dough can be applied to allow the user to work outside the range of the x-rays. For this purpose, a trocar or a cannula can be arranged as well on the hose. Said systems are known, for example, from U.S. Pat. No. 7,112,205 B2, U.S. Pat. No. 8,038,682 B2, U.S. Pat. No. 8,308,731 B2, DE 10 2005 045 227 A1, EP 1 074 231 B1, EP 1 596 736 B1, U.S. Pat. No. 9,005,209 B2, and WO 2008/097855 A2.

Alternatively, other set-ups can be used for keeping the user away from the x-rays, such as are described, for example, in documents U.S. Pat. Nos. 6,676,663 B2, 7,008,433 B2, 8,348,494 B2, EP1 464 292 B1, EP 1 614 403 B1, US 2008/319445 A9, and WO 2008/038322 A2.

A bone cement applicator for vertebroplasty for application of bone cement dough comprising a hose, a trocar, and a mixer is known from US 2008/0086143 A1. The bone cement applicator comprises two cartridges arranged next to each other, in which the starting components are stored as well. The bone cement applicator is assembled right before use. In bone cement applicators for vertebroplasty of this type, pressure is exerted on the starting components of the bone cement dough by means of an extrusion device propelling the dispensing plungers in the cartridges, and the pressure is used to expel the starting components from the cartridges and through the hose. In this context, the starting components are usually mixed first in an upstream static mixer. As a result, the parts of the bone cement applicator serving as borders to the bone cement flow (the cartridges, the housing of the mixer, and the hose) are subject to elastic deformation. When the propulsion of the dispensing plunger is stopped, the elastic force of said parts leads to a volume contraction of said parts such that bone cement dough continues to exit through the application opening of the hose and/or trocar. This may lead to contamination of the operation theatre or of the user with bone cement dough or an excessive amount of the bone cement dough is applied inadvertently. Moreover, when the volume flow of the bone cement dough is to be started up again, pressure needs to be established in the bone cement dough first to make the bone cement dough exit through the application opening. This, in turn, delays the time point after propulsion of the dispensing plungers from which the bone cement can actually be applied, which is also undesirable.

Since the bone cement dough and the starting components, if applicable, are highly viscous, all these effects are relatively strongly pronounced in bone cement applicators of this type. This can be counteracted by the use of massive and expensive metallic housing parts. Said parts need to be cleaned after use and need to be sterilised for further use or need to be recycled with much effort.

Accordingly, it is the object of the invention to overcome the disadvantages of the prior art. In particular, the invention is to provide a simple and inexpensively produced bone cement applicator for vertebroplasty for pasty multicomponent polymethylmethacrylate bone cements and a method for the application of a bone cement dough with a bone cement applicator for vertebroplasty with a simple design and being inexpensive to produce, whereby the bone cement dough does not continue to flow once the bone cement flow is stopped. Moreover, it shall be possible to reuse the bone cement applicator as soon as possible after interruption of the flow of bone cement dough. Contamination of the surroundings and of the user with bone cement dough shall be excluded to the extent possible.

In particular, the invention is based on the object to provide a simple bone cement applicator as a mixing and application system for a powder-liquid PMMA or just as an application system for vertebroplasty. It shall be possible to easily manufacture the bone cement applicator from plastic material and thus the bone cement applicator shall be suitable as a product for single use. It shall be possible to extrude the mixed bone cement dough with a conventional manually-operated extrusion device of the type that is hitherto conventional for use with PMMA bone cements for the cementing of knee and hip TEPs. The bone cement applicator is to be designed appropriately such that an immediate emergency stop of the flowing bone cement dough is feasible without contamination of the surgical theatre (operation theatre) by the bone cement dough taking place.

Moreover, it shall be feasible to ready the bone cement applicator as a ready-to-use system for single use in simple manner with a minimal number of assembly steps within a few seconds and, connected to manually drivable medical extrusion devices, the bone cement applicator is to generate a homogeneously mixed bone cement dough immediately after the manual actuation of the extrusion device commences, and the bone cement applicator is to dispense the homogeneously mixed bone cement dough at the application opening of a hose, if possible also if the flow of the bone cement dough was interrupted briefly. It shall be feasible to utilise the manually operated extrusion devices used thus far in operation theatres for the conventional polymethylmethacrylate bone cements, which possess one push rod each and/or one pestle each and, if applicable, one plunger cup each, for dispensation of the two-component polymethylmethacrylate bone cement and/or of the bone cement dough by means of the bone cement applicator to be developed. This is to eliminate the need to purchase special extrusion devices for dispensation of pasty two-component polymethylmethacrylate bone cements.

Preferably, the starting components of the bone cement dough are to be mixed with each other in the bone cement applicator. Alternatively, a bone cement dough mixed earlier or a pre-mixed bone cement dough can be used.

The bone cement applicator shall also allow a small volume of the homogeneously mixed bone cement dough of approximately 50 mL and/or maximally 80 mL to be dispensed without any substantial residual amounts (more than 20 mL) remaining in the system and needing to be discarded with great effort. More substantial volumes of the cement dough are usually not desired for applications in vertebroplasty.

The bone cement applicator shall be designed appropriately such that any confusion of the relevant assembly steps by the user is excluded to the extent possible by design means and such that the bone cement applicator can be used by largely untrained personnel as well. Moreover, a method for dispensation of a bone cement dough is to be provided, which preferably is also designed for the mixing of the starting components.

The objects of the invention are met by a bone cement applicator for application of a bone cement dough in the region of the spine, the bone cement applicator comprising a tubular cartridge with an internal space;
a dispensing plunger for expelling the starting components of the bone cement dough or the bone cement dough from the cartridge through an opening of the cartridge opposite from the dispensing plunger, whereby the dispensing plunger is mobile in longitudinal direction in the internal space of the cartridge;
a hose;
an application opening through which the bone cement dough is applicable; a three-way valve that is operable from outside and is arranged or arrangeable in the hose or on a side of the hose facing the cartridge, whereby the three-way valve is in fluid connection with the opening of the cartridge, when the three-way valve is connected to the cartridge; a collecting container arranged on the three-way valve for accommodation of bone cement dough,
whereby the three-way valve is appropriately designed and is appropriately arranged or arrangeable in the bone cement applicator such that it, being in a first position, provides a fluid connection between the application opening and the opening of the cartridge and closes a feed-through to the collecting container and,
being in a second position, provides a fluid connection between the application opening and the collecting container and closes a passage to the opening of the cartridge.

It is preferred according to the invention for the bone cement applicator to be designed for vertebroplasty and it can therefore be used and is well-suited for vertebroplasty.

According to the invention, it is preferred for the three-way valve to be operable by hand.

Preferably, the three-way valve is firmly connected to the hose.

Particularly preferably, the cartridge as well as the three-way valve with the hose or the three-way valve and the hose are present as single parts that is connectable to each other.

The invention can provide the hose to comprise the application opening, in particular a Luer system adapter or a trocar with the application opening, and/or to comprise a connecting opening that is situated opposite from the application opening.

The application opening is in fluid connection with the hose.

Being on the side of the cartridge shall be understood to mean that the arrangement is situated with respect to the flow direction of the bone cement dough and/or of the starting components with the three-way valve being in the suitable position, meaning on the side from which the bone cement dough and/or the starting components flow in, when the three-way valve is connected to the cartridge.

The three-way valve is arranged in the hose or on the end of the hose that is situated opposite from the application opening.

When the hose and the three-way valve are connected to the cartridge, the three-way valve or the end of the hose that is opposite from the application opening is in fluid connection with the opening of the cartridge.

Preferably, the invention can provide a tube or a tube with a mixer to be arranged or to be arrangeable between the cartridge and the three-way valve or between the cartridge and the end of the hose that is situated opposite from the application opening.

The dispensing plunger of the cartridge is preferably arranged in the end of the cartridge that is situated opposite from the opening of the cartridge.

The invention can provide a mixer for mixing of the bone cement dough, in particular a static mixer, to be arranged or to be arrangeable downstream from the opening of the cartridge or between the opening of the cartridge and the three-way valve or the hose, whereby the three-way valve preferably is arranged or arrangeable between the mixer and the hose, whereby the three-way valve, being in the first position, provides a fluid connection between the application opening and the mixer and, being in the second position, closes the passage to the mixer.

As a result, the starting components what the pre-mixed bone cement dough from the cartridge can be mixed better. In addition, due to the arrangement of the three-way valve according to the invention, the pressure of the bone cement dough in the mixer is maintained and therefore bone cement dough can be expelled again through the hose and the application opening right after the three-way valve is opened again without the pressure in the mixer having to be built up again. As a result, the bone cement dough can be provided more rapidly after the three-way valve is opened.

The present invention also proposes that the bone cement applicator is operable by means of a manually operated extrusion device and the dispensing plunger to be movable in the cartridge by manual force, whereby the cross-section of the internal space of the cartridge is maximally 3.5 $cm^2$, preferably is maximally 2.5 $cm^2$.

The dispensing plunger being movable in the cartridge by manual force shall be understood to mean that the dispensing plunger is movable in the cartridge by means of a manually driven extrusion device.

Due to the maximum cross-sectional and/or propulsion areas, which limit the force required for expulsion and mixing of the starting components of the bone cement dough, being as specified above, the viscous bone cement dough can be expelled from the cartridge through the hose and, if applicable, through the mixer by manual force. As a result, a manually driven and/or drivable bone cement applicator can be provided that works without having a connection for an external energy source and without having an internal energy source and therefore is ready for use at all times and independent of the external circumstances, and/or an extrusion device that works without a connection for an external energy source and also without an internal energy source and therefore is ready for use at all times and independent of the external circumstances can be used.

Moreover, the invention can provide at least part of the hose to be flexible and/or the application opening to be arranged in a connection with an internal thread, in particular in a Luer system adapter, or in a trocar.

As a result, the bone cement applicator can also be used in regions that are difficult to access. Moreover, the hose and, if applicable, the trocar, allow the input of bone cement dough to be monitored with an x-ray procedure without the user of the bone cement applicator being directly exposed to the x-rays. The trocar can be connected to the remainder of the hose by means of an internal thread, in particular by means of a Luer system. Having a Luer system adapter in place makes the bone cement applicator and/or the components thereof universally connectable.

Preferably, the invention can just as well provide the collecting container to be impermeable for the bone cement dough towards the outside, preferably the collecting container to be fluid-tight or fluid-tight and gas-tight, and/or the collecting container to have a volume that is at least as large as half the volume of the hose, preferably is at least as large as the volume of the hose.

As a result, the bone cement dough and its components can be prevented from being pushed outwards and from thus soiling and/or contaminating the surgical theatre or the user.

Moreover, the invention can provide the cartridge to comprise, on its rear side, an attachment element for attachment of an extrusion device.

This enables a stable attachment of the extrusion device to the bone cement applicator.

Preferred embodiments of the present invention are characterised in that the cartridge, the dispensing plunger, the three-way valve, and the hose and, if applicable, the mixer, are made from plastic material, whereby polyethylene-co-vinylalcohol (EVOH), polybutylene-terephthalate (PBT), polyethylene-terephthalate (PET), and polymethacrylic acid methylester-co-acrylonitrile are preferred as plastic materials.

The design with plastic materials is inexpensive and easy to implement. The preferred plastic materials are particularly well-suited due to their resistance with respect to the chemicals contained in the starting components and in the bone cement dough.

The cartridge comprises a cylindrical internal space and/or the dispensing plunger closes off in fluid-tight manner against the internal walls of the cartridge, preferably closes off tightly against the internal wall of the cartridge by means of at least one circumferential seal and/or a wiper lip.

According to a preferred refinement, the present invention can provide the opening of the cartridge to be arranged in a cartridge head, in particular in a cartridge head that is detachably connected to the cartridge, whereby an attachment means, in particular an external thread, is provided in the region of the opening by means of which the hose or the three-way valve is connected or connectable to the cartridge, in particular is connected or connectable in pressure-tight manner by means of a sealing means.

By this means, the hose or the three-way valve or a tube connected to the three-way valve or the hose can be connected easily to the cartridge right before use of the cartridge.

The invention can just as well provide a mixing facility to be provided by means of which the content of the cartridge is mixable in the internal space of the cartridge, whereby the mixing facility can preferably be operated from outside when it is connected to the cartridge.

By this means, the starting components can be mixed or pre-mixed in the cartridge to form the bone cement dough. This provides for the opportunity to mix the bone cement dough in a vacuum (or in a negative pressure), by evacuating the internal space of the cartridge by means of a vacuum connector, which is particularly preferred according to the invention. In this context, it is preferred to provide a pore disk to be present in the connection of the vacuum connector to the internal space of the cartridge, whereby the pore disk is impermeable for cement powder.

Bone cement applicators equipped with a mixing facility can be provided to have multiple mixing vanes, connected to a mixing rod, arranged in the internal space of the cartridge, and these to be movable through a motion of the mixing rod, in particular through axial linear motion and through rotation of the mixing rod, in the internal space of the cartridge in order to mix starting components in the internal space of the cartridge, when the mixing facility is connected to the cartridge.

By this means, it is particularly easy to mix the bone cement dough by hand. Moreover, the condition of the bone cement dough during the mixing process can be recognised by way of its consistency.

Moreover, the invention can provide the mixing facility, in particular the mixing rod of the mixing facility, to be guided through the opening of the cartridge into the internal space of the cartridge, whereby the mixing facility is removable from the cartridge, preferably is drawable out of the cartridge, when it is connected to the cartridge.

Then, the mixing facility is removable after the bone cement dough is formed by mixing from the starting components and before application of the bone cement dough and preferably can be replaced by the hose and the three-way valve and, if applicable, in addition the trocar and a mixer.

The objects underlying the present invention are also met by a method for application of a bone cement dough, in particular of a pasty multicomponent polymethylmethacrylate bone cement dough, with a bone cement applicator according to the invention, comprising the following steps proceeding in the order given:

a) filling a bone cement dough into the internal space of the cartridge or filling the starting components of the bone cement dough into the internal space of the cartridge;

b) inserting the bone cement applicator into an extrusion device, whereby the extrusion device comprises an axially propellable pestle for propulsion of the dispensing plunger in the internal space of the cartridge in the direction of the opening of the cartridge;

c) moving the three-way valve to the first position or the three-way valve being in the first position and extruding the content of the cartridge by means of the extrusion device by axial propulsion of a pestle of the extrusion device, whereby the pestle pushes the dispensing plunger in the direction of the opening, by means of which the bone cement dough is pushed through the hose and out of the application opening or whereby the starting components are mixed to form the bone cement dough and the bone cement dough is subsequently pushed through the hose and out of the application opening;

d) moving the three-way valve to the second position;

e) whereby the three-way valve, in the second position of the three-way valve, stops the flow of the bone cement dough or of the starting components out of the cartridge into the hose and part of the bone cement dough in the hose that is pressurised between the application opening and the three-way valve is pushed through the three-way valve into the collecting container.

If the three-way valve is not connected to the cartridge already, the three-way valve with the hose (and, if applicable, with a static mixer and/or a trocar) is connected to the cartridge before step c).

In this context, the invention can provide the three-way valve to be moved to the first position again in a step f) after step e) and, by this means, the bone cement dough to be guided again out of the cartridge through the three-way valve to the application opening, whereby it is preferred for steps d), e), and f) to be repeated once or multiple times in the order given.

While the three-way valve is closed, i.e. while it is in the second position, it is expedient to stop the propulsion of the pestle and thus the propulsion of the dispensing plunger and to resume the propulsion only once the three-way valve is in the open first position again.

Moreover, the invention can provide the extrusion device to be driven manually, by compressed air or by a motor, whereby the manual force, the compressed air or the motor propels the pestle in the direction of the opening of the cartridge.

Manually drivable extrusion devices are preferred according to the invention, since they do not need to be connected to a source of compressed air or an energy source and do not need to contain this kind of source.

Referring to the first embodiment, the invention can provide the pestle of the extrusion device to push onto the side of the dispensing plunger facing away from the opening of the cartridge, and the dispensing plunger to be driven by the pestle.

A cup can be arranged on the end of the pestle of the extrusion device that faces in the direction of the cartridge, and the cup is usable to push onto the dispensing plunger in order to propel the dispensing plunger in the cartridge.

The invention can just as well provide the starting components or the bone cement dough to be filled into the internal space of the cartridge in step a) and the starting components or the bone cement dough to be pressed out of the cartridge in step c), preferably the starting components or the pre-mixed bone cement dough to be pressed through a static mixer that is arranged between the hose or the three-way valve and the opening, whereby the starting components preferably are mixed in the mixer to form a bone cement dough.

Moreover, the invention can provide the starting components to be filled into the internal space of the cartridge in step a) and to be mixed in the internal space of the cartridge with a mixing facility ahead of step b), whereby the hose with the three-way valve is then attached to the cartridge, in particular at the opening of the cartridge, whereby the mixing facility preferably is removed from the cartridge before the hose with the three-way valve is connected.

The invention is based on the surprising finding, that the pressure acting on the bone cement dough in the hose and, if applicable, in the trocar can be relieved without any substantial amount of the bone cement dough continuing to flow out of the application opening by adjusting a three-way valve that is connected to a collecting container, a hose, and at least one cartridge. Simultaneously, this allows the pressure of the bone cement dough and, if applicable, of the starting components in the cartridge to be maintained all the way to the three-way valve and, in particular, in the mixer as well (if any is present). As a result, the lapse of time between opening of the three-way valve (after moving it to the first position) to the resumed exit of the bone cement dough out of the application opening on the tip of the hose or trocar is very short. Accordingly, the pressure of the bone cement applicator is maintained between the three-way valve and the dispensing plunger, when the three-way valve is closed (in the second position of the three-way valve), whereas rapid pressure relief of the bone cement applicator is attained between the three-way valve and the application opening since the bone cement dough flows off through the three-way valve in the second position. To ensure that the bone cement dough does not contaminate the surroundings or the user, a collecting container is provided that prevents the bone cement dough exiting through the three-way valve from dripping. Preferably, the collecting container is closed for this purpose. Theoretically, it may be sufficient to retain the bone cement dough. The collecting container can just as well be flexible and/or elastic and can expand when it takes up the bone cement dough exiting from the three-way valve.

The particular advantage of the bone cement applicator according to the invention is that conventional manually-driven extrusion devices that are common for normal PMMA cements can be used to press the two-component spine cement and/or the two-component bone cement dough for vertebroplasty through a thin hose into the trocar. The augmentation of vertebral bodies takes place under permanent x-ray control. Having a hose between the trocar and the applicator allows the physician to not have to work with his or her hands within the range of the x-rays. No complex expensive hydraulic application devices are required in this context. Moreover, it is advantageous for the bone cement applicator to contain an emergency relief valve in the form of a three-way valve by means of which the extrusion process can be stopped immediately once the cement dough starts to flow into undesired regions of the vertebral bodies. Said emergency relief valve acts as a pressure relief for the application system, in which the trailing pressure of the cement dough from the static mixer is blocked and simultaneously the cement dough situated upstream of the emergency relief valve is relieved of pressure, by opening a channel leading into the collecting container into which the cement dough can exit until the pressure in the hose and/or in the trocar is relieved. Due to the collecting container, the surgical theatre and/or the gloves of the physician are not contaminated by the bone cement dough exiting at the emergency relief valve.

Own experiments have shown that a very large pressure drop occurs in the hose, but, in particular, also on a static mixer (if any is present) during the extrusion process of the cartridge due to the high viscosity of the pasty starting components.

Furthermore, the invention is based on observing that highly viscous cement dough can be dispensed from cylindrical cartridges through a static mixer and the hose using commercial, manually-driven extrusion devices in an acceptable amount of time and with an application of force that is acceptable since it can be applied manually, if the diameter of the dispensing plunger on its front side is maximally 35 mm. The design according to the invention provides a bone cement applicator that can realise such small diameters for the application of highly viscous bone cement doughs. In this context, the cartridge can still be filled with the starting components without too much effort.

An exemplary bone cement applicator is composed of
1. a tubular cartridge with an internal diameter that is less than or equal to 20 mm (preferably 15 mm);
2. a dispensing plunger;
3. a manually-removable cartridge head with a mixing element that is arranged therein such as to be axially mobile and be operable from outside;
7. a three-way valve (as an emergency relief valve) on the cartridge head (more specifically, that can be attached to and arranged on the cartridge head) with a lateral emergency relief opening;
8. a hollow reservoir (the collecting container) that is arranged appropriately about the emergency relief valve (the three-way valve) such that the emergency relief opening is connected to the hollow space of the reservoir; and
9. a hose that is connected, on one end, to the emergency relief valve and, on the other hose end, to a Luer system adapter.

BRIEF DESCRIPTION OF THE DRAWINGS

Further exemplary embodiments of the invention shall be illustrated in the following on the basis of seventeen schematic figures, though without limiting the scope of the invention. In the figures.

DETAILED DESCRIPTION OF THE DISCLOSURE

For purposes of simplification, the same reference numbers are used for identical components in the figures even if the embodiments are different.

Figure 1:
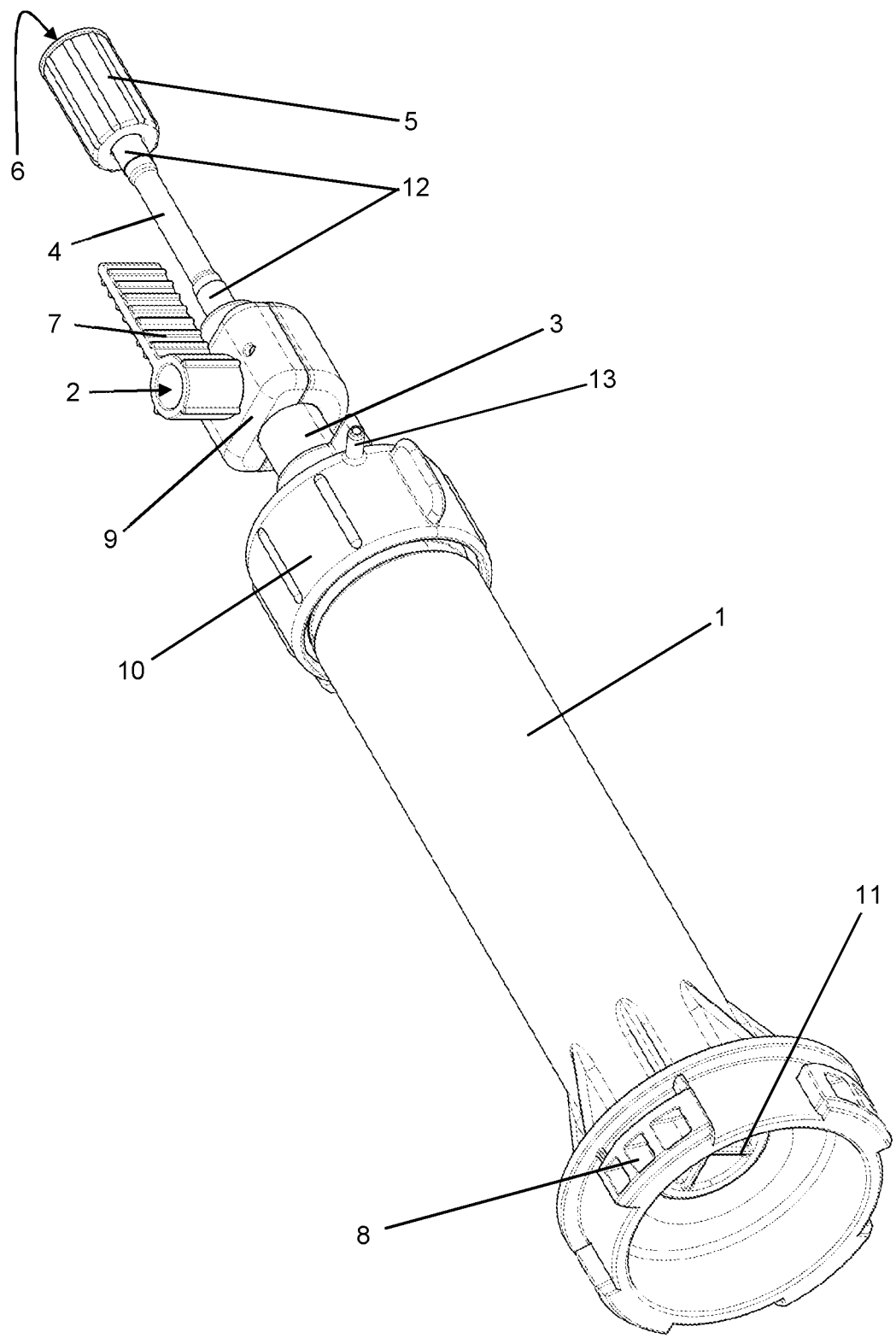
FIG. 1: shows a schematic perspective view of an exemplary bone cement applicator according to the invention.

FIGS. 1 to 6 show an exemplary bone cement applicator according to the invention for vertebroplasty. FIG. 1 shows a schematic perspective view of an exemplary bone cement applicator according to the invention. The bone cement applicator comprises a cartridge 1, a three-way valve 2, a tube 3, and a hose 4. The tube 3 preferably is an attachment of the three-way valve 2, but can just as well be considered to be a part of the three-way valve 2. The starting components of the bone cement dough to be produced or a ready-mixed bone cement dough can be filled into a cylindrical internal space (not shown in FIG. 1) of the cartridge 1, and/or preferably have already been filled in and mixed in the design shown in FIG. 1. The bone cement applicator shown is not designed for and, to be exact, not suitable for storage of the starting components. The cartridge 1 was opened shortly before use and connected to the three-way valve 2, the tube 3, and the hose 4 of the bone cement applicator after the bone cement dough was filled into the cartridge 1 or after the starting components were mixed in the cartridge 1 to form a bone cement dough.

A Luer system adapter 5, in which an application opening 6 is situated, is arranged on the front side of the hose 4. A trocar (not shown in FIG. 1) or a cannula or any other extension with a fitting Luer system connector for application of the bone cement dough in the region of the vertebrae is connectable to said Luer system adapter 5. The trocar can be considered to be part of the bone cement applicator. The application opening 6 is extended correspondingly by the trocar, i.e. the application opening 6 is extended to the tip of the trocar by connecting the trocar. Usually, the bone cement applicator is not operated and used in the absence of the trocar.

The three-way valve 2 can be manually operated by means of a T-handle 7 by turning it by 90° and thus transitioning it from a closed position to an opened position or from a closed setting to an opened setting.

The rear side of the cartridge 1 and/or the floor of the cartridge has a connector 8 for connecting an extrusion device (not shown) arranged on it. The extrusion device is to be connected to said connector 8 in order to extrude the content of the cartridge 1, i.e. the bone cement dough from the cartridge 1, then in flow direction through the tube 3, through the (opened) three-way valve 2, and through the hose 4 (and preferably through the trocar) and through the application opening 6 by means of which the bone cement is applied in the vertebra.

A collecting container 9 is arranged in the area of the three-way valve 2 and surrounds the three-way valve 2 axially with respect to the longitudinal axis of the bone cement applicator. The collecting container is plugged together from two plastic parts (see FIGS. 2 and 3).

The cartridge 1 and the tube 3 are connected to each other at a union nut 10. An external thread fitting the internal thread of the union nut 10 is provided on the cartridge 1, in the region of the cartridge head 10 that is opposite from the cartridge floor, such that the union nut 10 can be screwed onto it by means of the internal thread. The tube 3 is connected to the cartridge 1 by being screwed onto a socket 32 (see FIGS. 7, 8, 10 and 12 to 17) on the union nut 10. The tube 3 comprises an internal thread on its floor side for this purpose. Preferably, a seal is provided between the tube 3 and the cartridge 1. Before the cartridge 1 is being connected to the tube 3 by means of the union nut 10, a mixing facility (see FIGS. 8, 9, 13, and 14) by means of which the content of the cartridge 1 can be mixed can be guided through the union nut 10.

A dispensing plunger 11 by means of which the content of the cartridge 1 can be propelled into the tube 3, out of the cartridge 1, is inserted into the cartridge 1. For this purpose, the dispensing plunger 11 needs to be pushed in the longitudinal direction in the internal space of the cartridge 1, in the direction of the union nut 10. A manually-driven extrusion device can be used for this purpose.

The three-way valve 2 and the Luer system adapter 5 are connected to the hose 4 in pressure-tight manner by means of a crimp connector using sleeves 12 made of metal. With the exception of the crimp connector, all parts of the bone cement applicator can be made from plastic material, whereby all seals preferably are made from elastic plastic material, such as, e.g., rubber.

The union nut 10 has a vacuum connector 13 provided on it through which the inside of the cartridge 1 and/or the internal space of the cartridge 1 can be evacuated.

Figure 2:
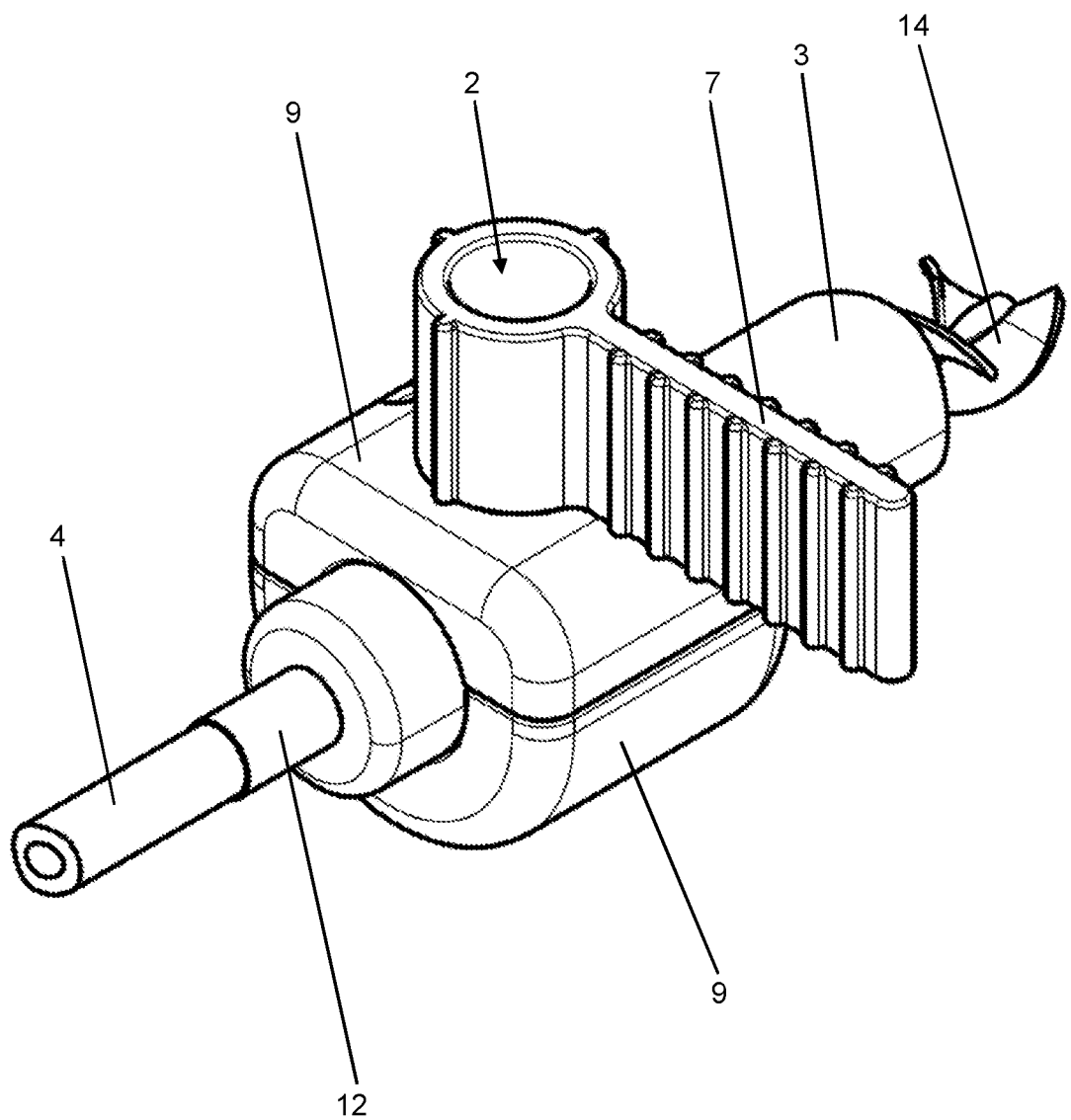
FIG. 2: shows a schematic perspective view of a magnified detail, in which the three-way valve of the bone cement applicator according to FIG. 1 is shown.
Figure 3:
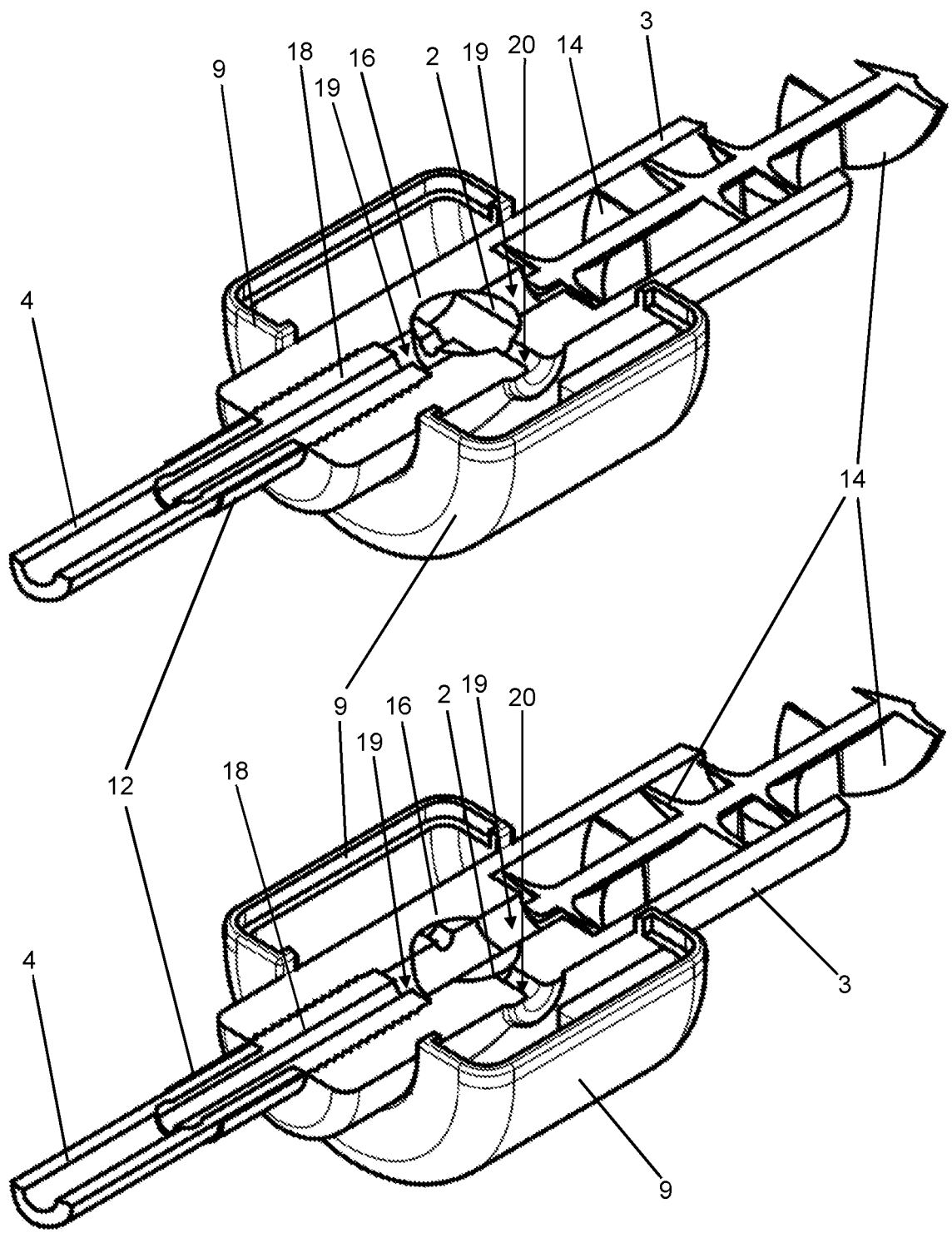
FIG. 3: shows two schematic perspective cross-sectional views through the three-way valve of the bone cement applicator according to FIGS. 1 and 2, namely the three-way valve in closed position (FIG. 3 top) and in open position (FIG. 3 bottom)
Figure 4:
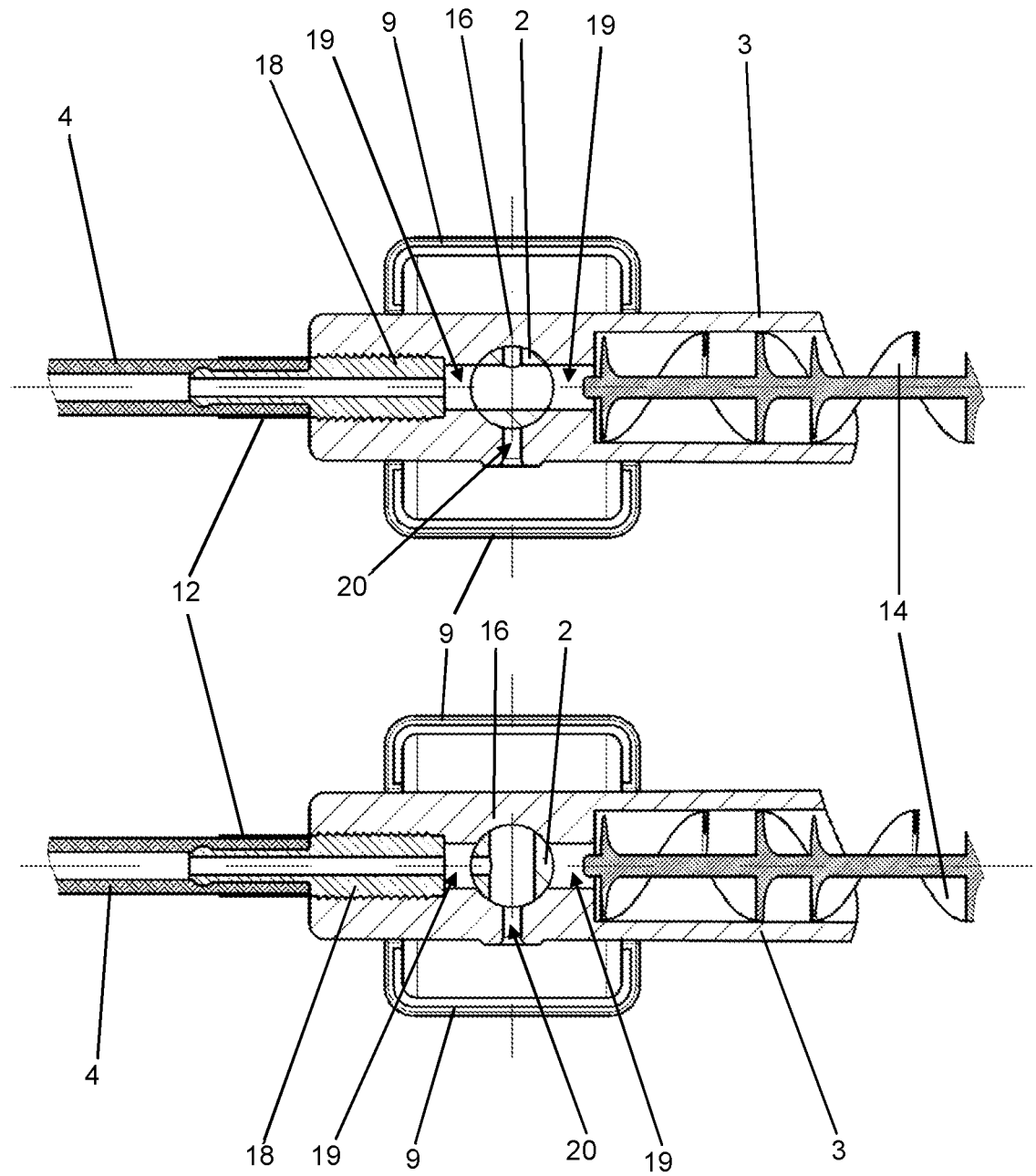
FIG. 4: shows two schematic top views of cross-sectional views through the three-way valve of the bone cement applicator according to FIGS. 1 and 2, namely the three-way valve in open position (FIG. 4 top) and in closed position (FIG. 4 bottom)
Figure 5:
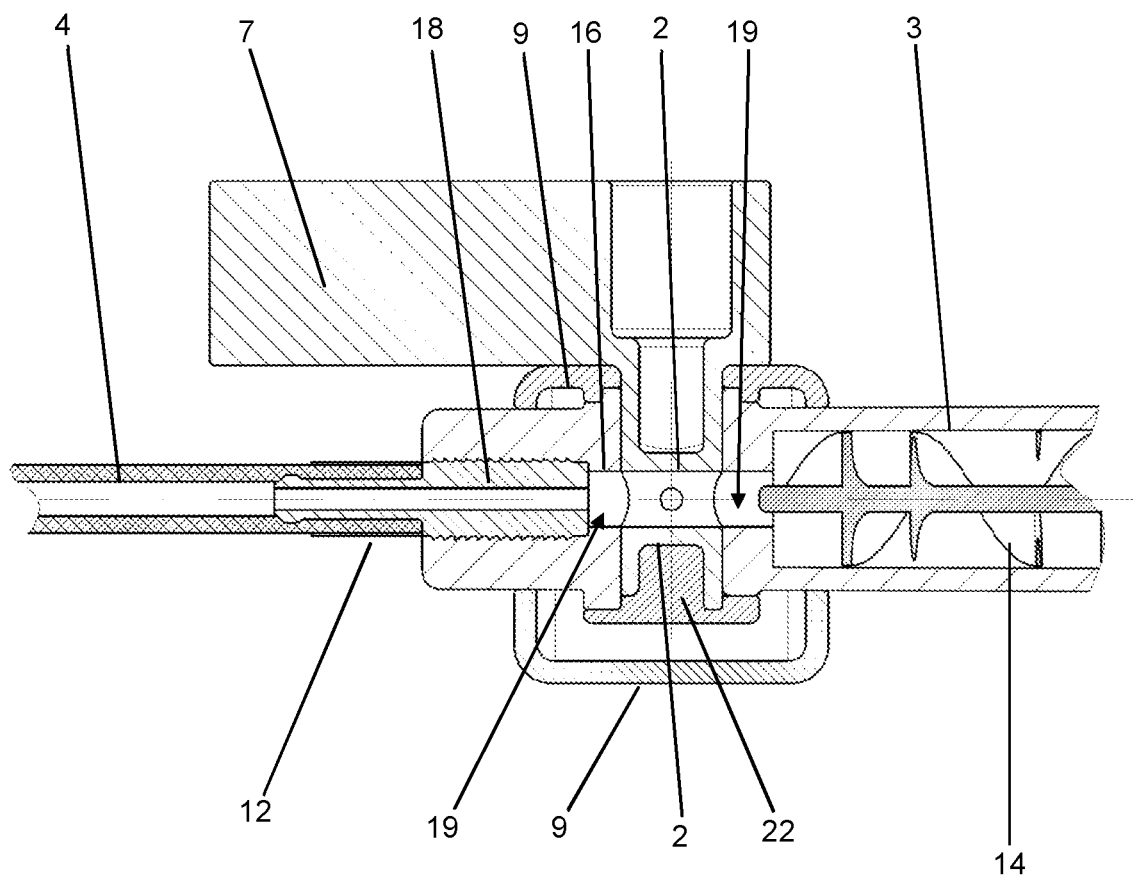
FIG. 5: shows a schematic cross-sectional view of the open three-way valve according to FIGS. 2, 3, and 4 of the bone cement applicator, whereby the sectional plane is selected to be perpendicular to the sectional planes according to FIGS. 3 and 4.

The main part of the bone cement applicator that is essential to the invention is, aside from the cartridge 1, mainly the three-way valve 2 and/or, in particular, the mode of function of the three-way valve 2 together with the collecting container 9 and with the channels formed on the inside of the bone cement applicator. FIG. 2 shows a schematic perspective view of a magnified detail, in which the three-way valve 2 of the bone cement applicator according to FIG. 1 is shown. FIGS. 3 and 4 show cross-sectional views through the three-way valve 2 of the bone cement applicator according to FIGS. 1 and 2, namely the three-way valve 2 in closed position (FIG. 3 top and FIG. 4 bottom) and in open position (FIG. 3 bottom and FIG. 4 top) for illustration of the mode of function of the three-way valve 2 by means of the internal design. Moreover, FIG. 5 shows a schematic cross-sectional view of the open three-way valve according to FIGS. 2, 3, and 4 of the bone cement applicator, whereby the sectional plane is selected to be perpendicular to the sectional planes according to FIGS. 3 and 4.

A static mixer 14 that extends all the way up to the three-way valve 2 is situated on the inside of the tube 3. The static mixer 14 is used to mix the starting components of the bone cement and/or the pre-mixed bone cement dough, when these are pressed through the static mixer 14 in the tube 3. However, since the starting components of the bone cement dough are preferably mixed in the internal space of the cartridge 1 by means of a hand-driven mixing facility or since a ready-mixed bone cement dough is being filled into the cartridge 1, there is preferably no static mixer 14 arranged in the tube 3. Accordingly, preferably there is no static mixer 14 present.

The rotatable three-way valve 2 is sectioned in the plane of symmetry of the channels seen therein in the cross-sectional views according to FIGS. 3 and 4. Accordingly, the channels are cylindrical and continue in the cut-off part of the three-way valve 2 in mirror-symmetrical manner. The channels form a T-part in the three-way valve 2. The three-way valve 2 rests in a fitting valve seat 16 that touches tightly against the three-way valve 2 and thus seals the channels, when these are rotated into the valve seat 16. The valve seat 16 has two passages 19 situated in it by means of which the larger through-going channel in the three-way valve 2 can be connected in fluid-tight manner to the tube 3 on one side and to an insert 18 made of metal for attachment of the hose 4 on the other side.

A feed-through 20 connecting the valve seat 16 to the inside of the collecting container that is closed towards the outside is situated perpendicular to the axis of the two passages 19. The valve seat 16 and the tube 3 are provided as a single part made of plastic material. In the open position of the three-way valve 2 (FIG. 3 bottom, FIG. 4 top, and FIG. 5), the large through-going channel is connected to the two passages 19 and the small perpendicular channel in the three-way valve 2 is closed through the valve seat 16. Accordingly, the bone cement dough from the cartridge 1 can flow from the tube 3 through the three-way valve 2 and the insert 18 into the hose 4. In the closed position of the three-way valve 2 (FIG. 3 top and FIG. 4 bottom), one side of the large through-going channel is connected to the feed-through 20 to the internal space of the collecting container 9 and the smaller perpendicular channel is connected to the passage 19 to the hose 4, whereas the other passage 19 to the mixing tube 3 is closed by the three-way valve 2. Accordingly, the bone cement dough can flow from the hose 4 and, if applicable, the trocar connected to the Luer system adapter 5 into the collecting container 9. The pressure for this purpose results from an elastic deformation of the hose 4 and, if applicable, trocar that has built up during the extrusion and/or while the bone cement dough was pressed through.

Being cylindrical on the outside, the three-way valve 2 is guided through a cylindrical borehole in the valve seat 16 and is connected to a stopper 22 on the side opposite from the T-handle 7 and thus is secured against dropping out or against being inadvertently pulled out of the valve seat 16.

Due to the design according to the invention, it is feasible to rapidly interrupt the flow of bone cement dough by rotating and thus closing the three-way valve 2 without large amounts of the bone cement dough continuing to flow through the application opening 6. Simultaneously, leakage of the bone cement dough and thus contamination of the surroundings or user is prevented by means of the collecting container 9 that takes up any excess of bone cement. Moreover, the pressure in the rear side of the bone cement applicator, i.e. between the three-way valve 2 and the dispensing plunger 11 in cartridge 1, is maintained such that the flow of bone cement dough can be provided again rapidly after the three-way valve 2 is opened again without the pressure having to be built up again in the rear side of the bone cement applicator.

Figure 6:
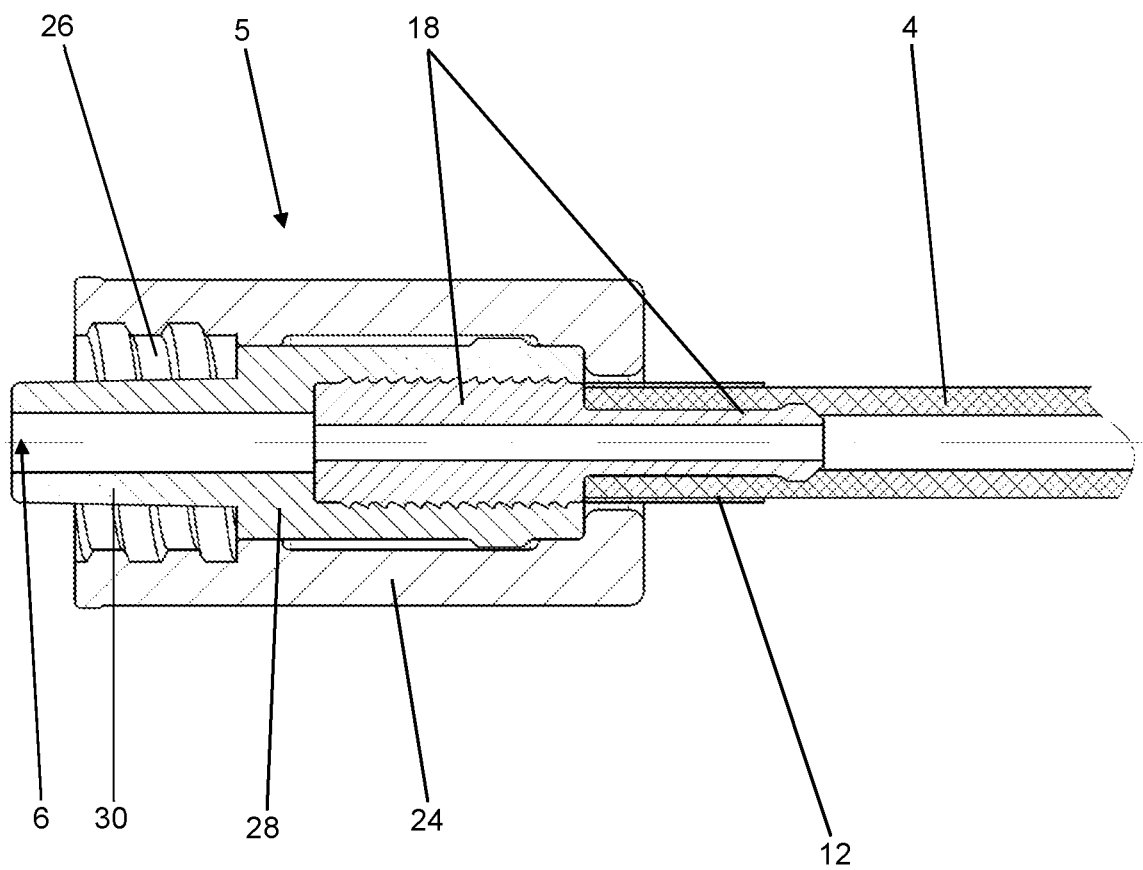
FIG. 6: shows a schematic cross-sectional view of the Luer system adapter on the tip of the bone cement applicator of the magnified detail.

FIG. 6 shows a schematic cross-sectional view of the Luer system adapter 5 on the tip of the bone cement applicator as a magnified detail view. Analogous to the connection of the valve seat 16 to the hose 4, an insert 18 made of a metallic material is situated in the Luer system adapter 5. The hose 4 is crimped to said insert 18 by means of the sleeve 12 in order to produce a pressure-tight connection. In addition, the Luer system adapter 5 consists of an external sleeve 24 with an internal thread 26 and an internal part 28 with a cone 30. A channel that is connected to the hose 4 via a channel of the insert 18 and merges into the application opening 6 on the other side extends inside the internal part 28. The external sleeve 24 and the internal part 28 are produced from plastic material. Theoretically, a different adapter can be provided as well or a trocar or similar component can be firmly connected to the hose 4.

For the viscous bone cement dough to be extrudable with a manually operated extrusion device, i.e. to be extrudable by manual force, the internal diameter of the cartridge 1 is selected to not be too large. Preferably, the internal diameter is less than 35 mm, particularly preferably less than 25 mm. As a result, the resistance caused by the viscous bone cement dough in the bone cement applicator is not so large that the bone cement can no longer be extruded by manual force by normal users.

Figure 7:
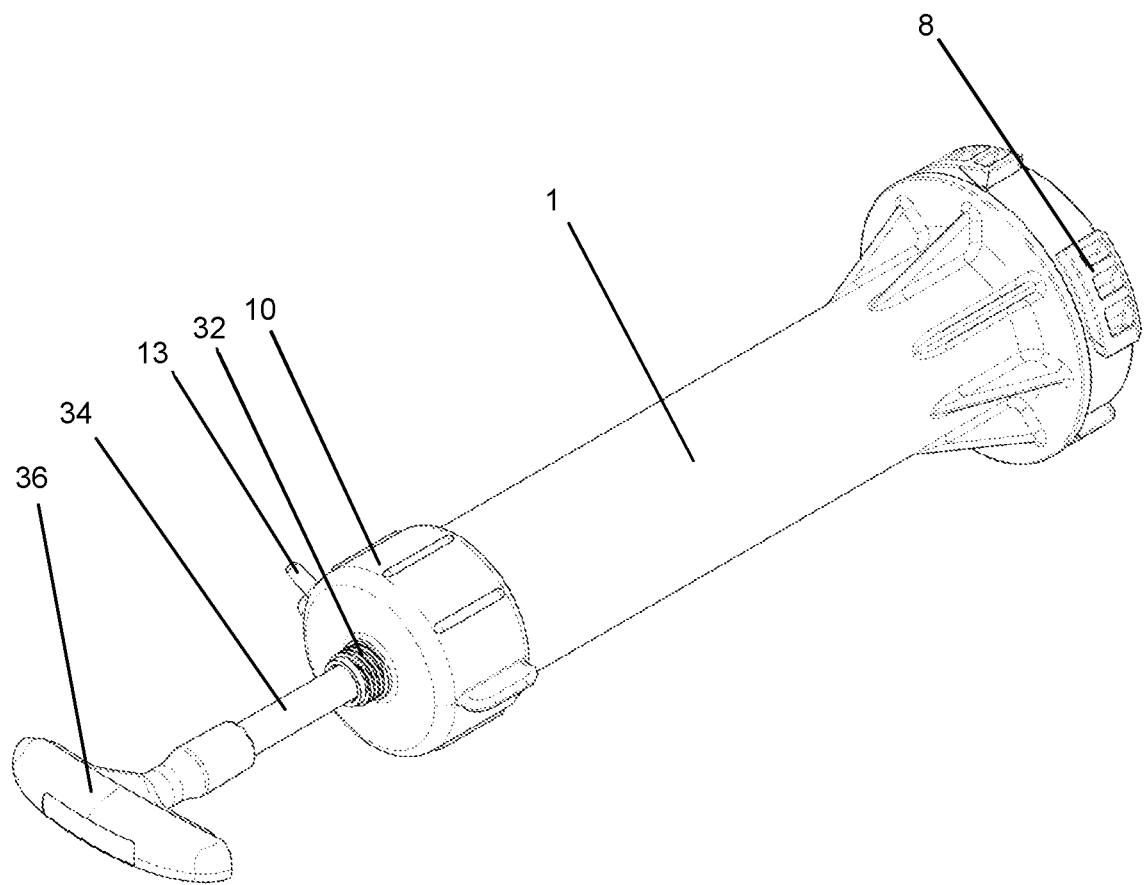
FIG. 7: shows a schematic perspective view of an exemplary bone cement applicator according to the invention, in the starting condition.
Figure 8:
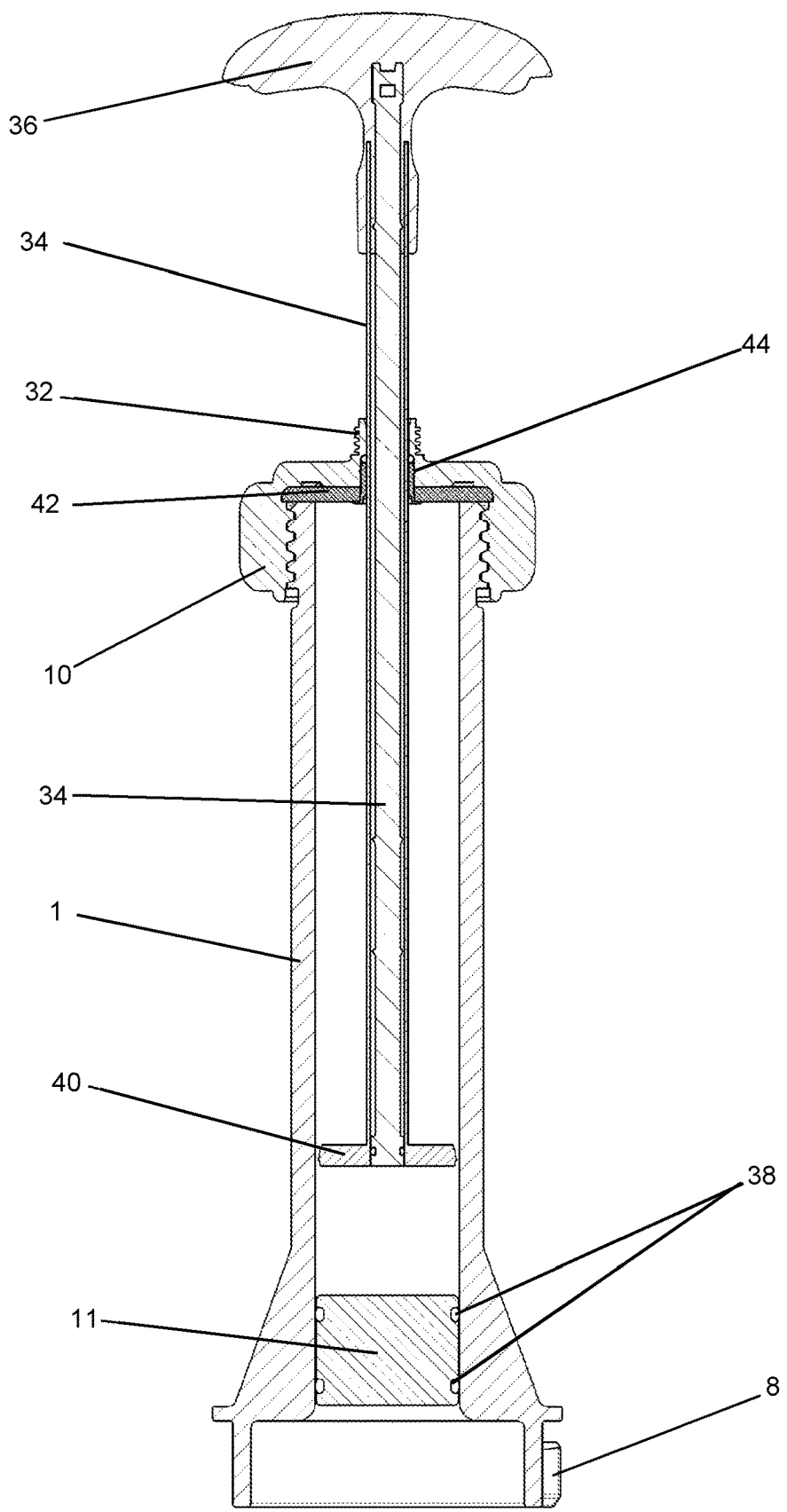
FIG. 8: shows a schematic cross-sectional view in longitudinal direction of the bone cement applicator according to FIG. 7.
Figure 9:
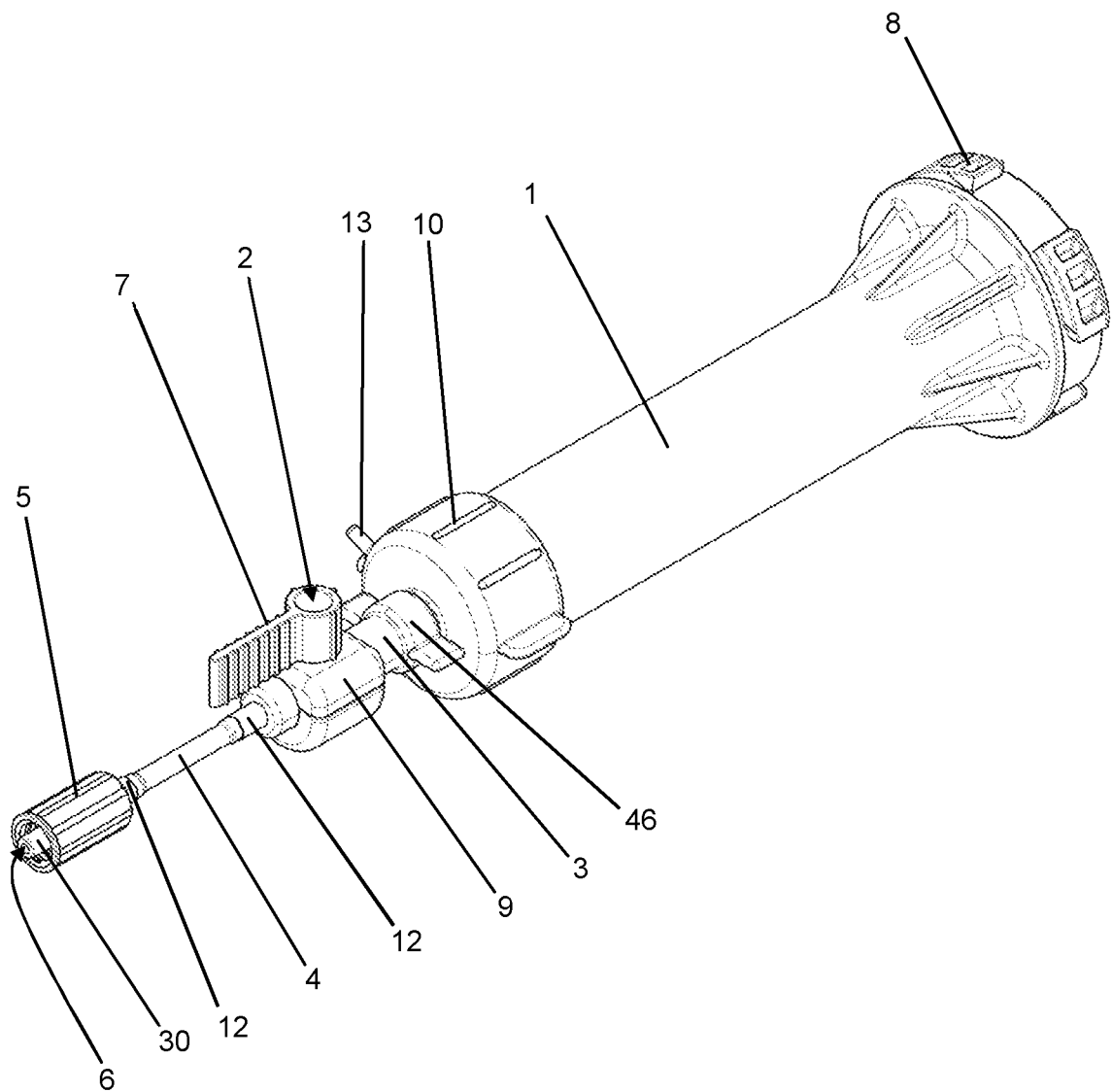
FIG. 9: shows a schematic perspective view of a bone cement applicator according to the invention, with three-way valve placed on it.
Figure 10:
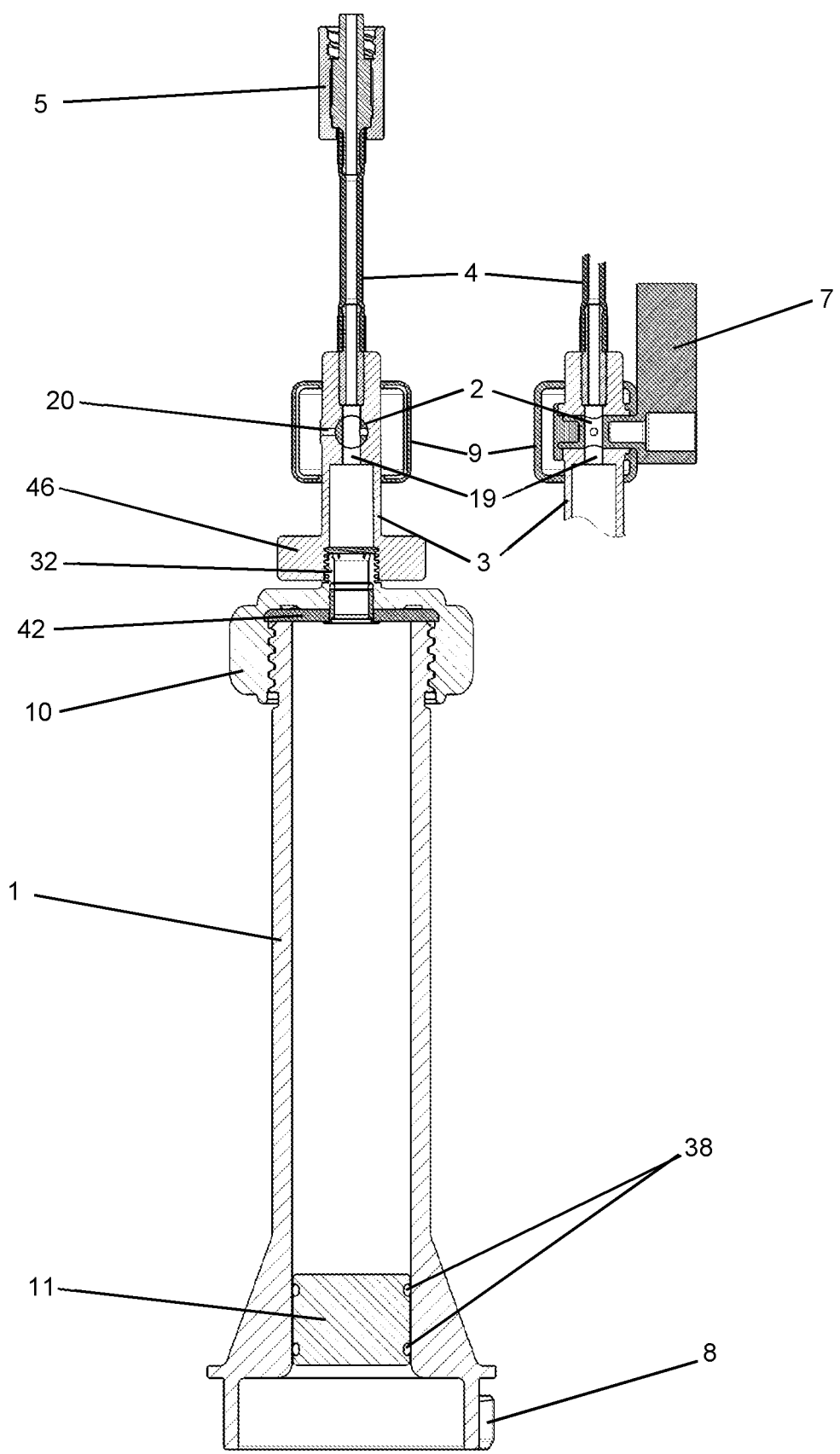
FIG. 10: left, shows a schematic cross-sectional view in longitudinal direction of the bone cement applicator according to FIG. 9 and, right, a detail with a perpendicular cross-section in longitudinal direction.
Figure 11:
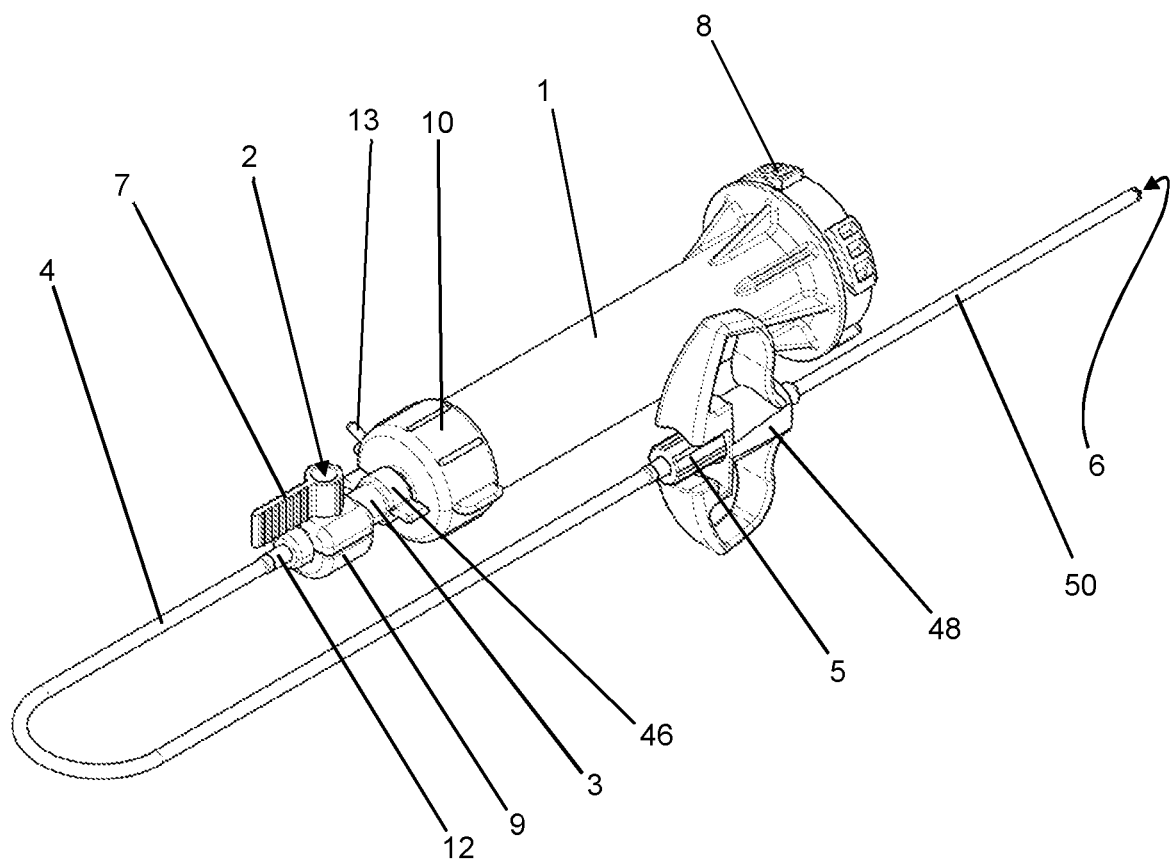
FIG. 11: shows a schematic perspective view of a bone cement applicator according to the invention, ready for application.
Figure 12:
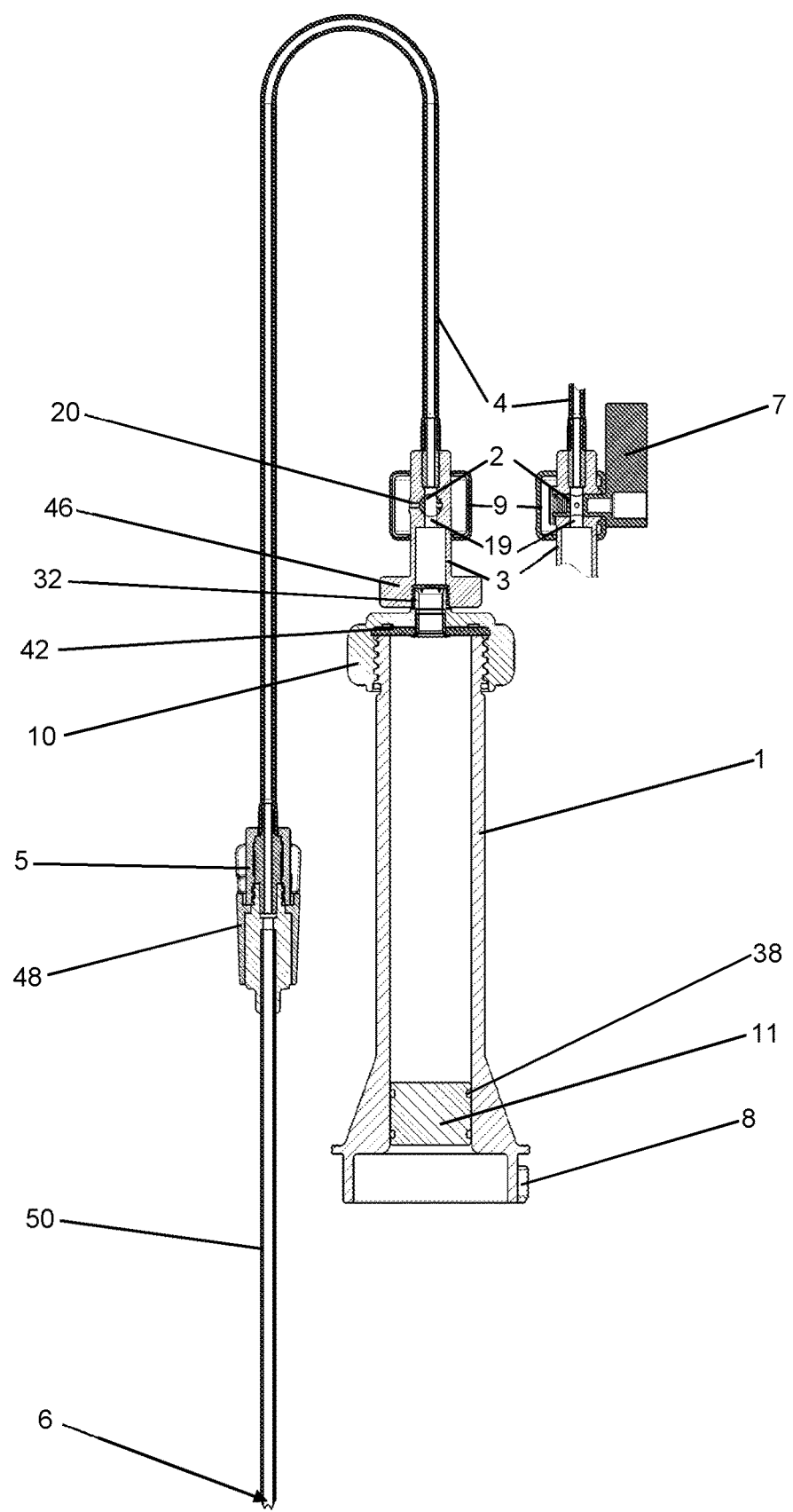
FIG. 12: left, shows a schematic cross-sectional view in longitudinal direction of the bone cement applicator according to FIG. 11 and, right, a detail with a perpendicular cross-section in longitudinal direction.
Figure 13:
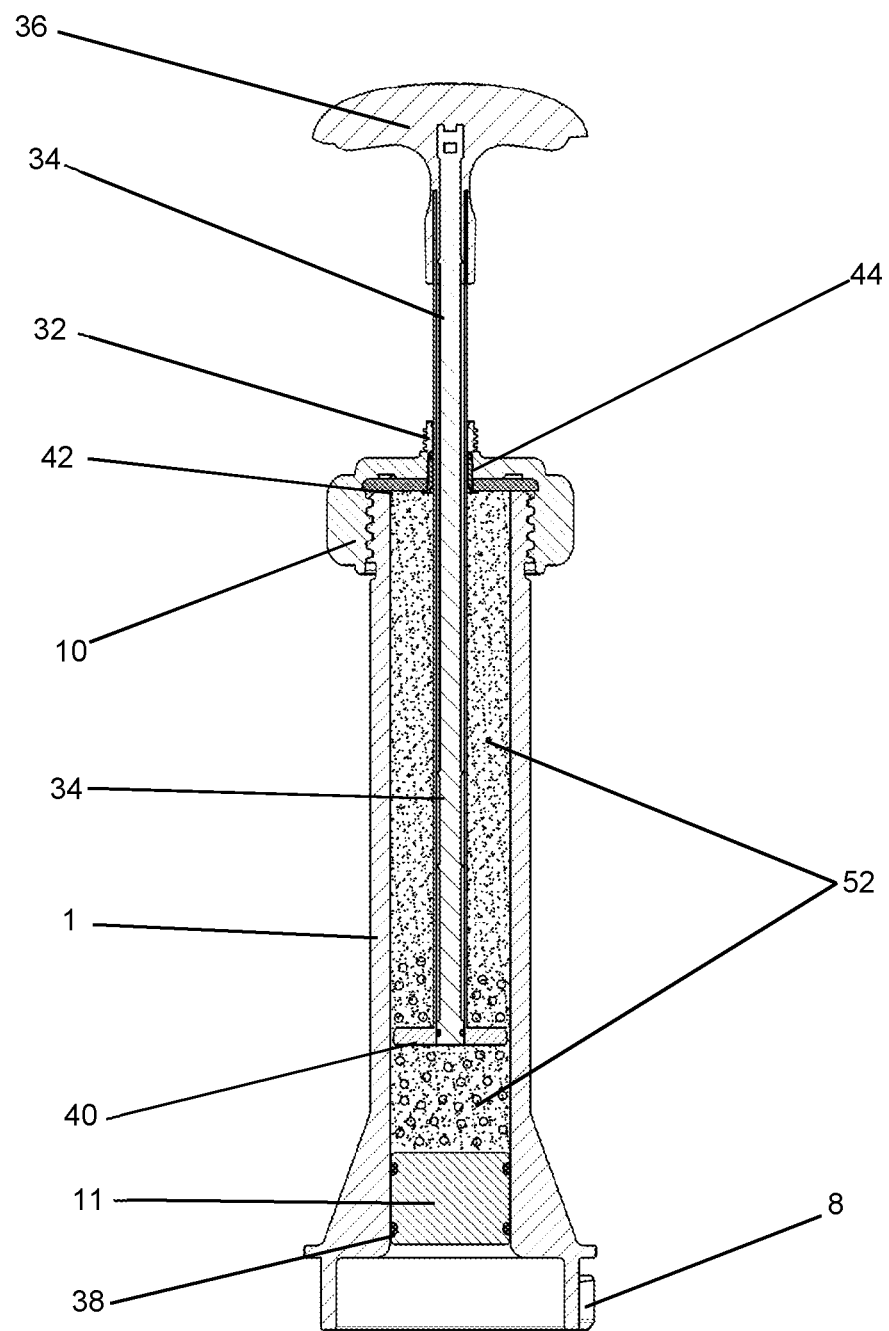
FIG. 13: shows a schematic cross-sectional view of a filled bone cement applicator according to the invention, prior to the mixing process.
Figure 14:
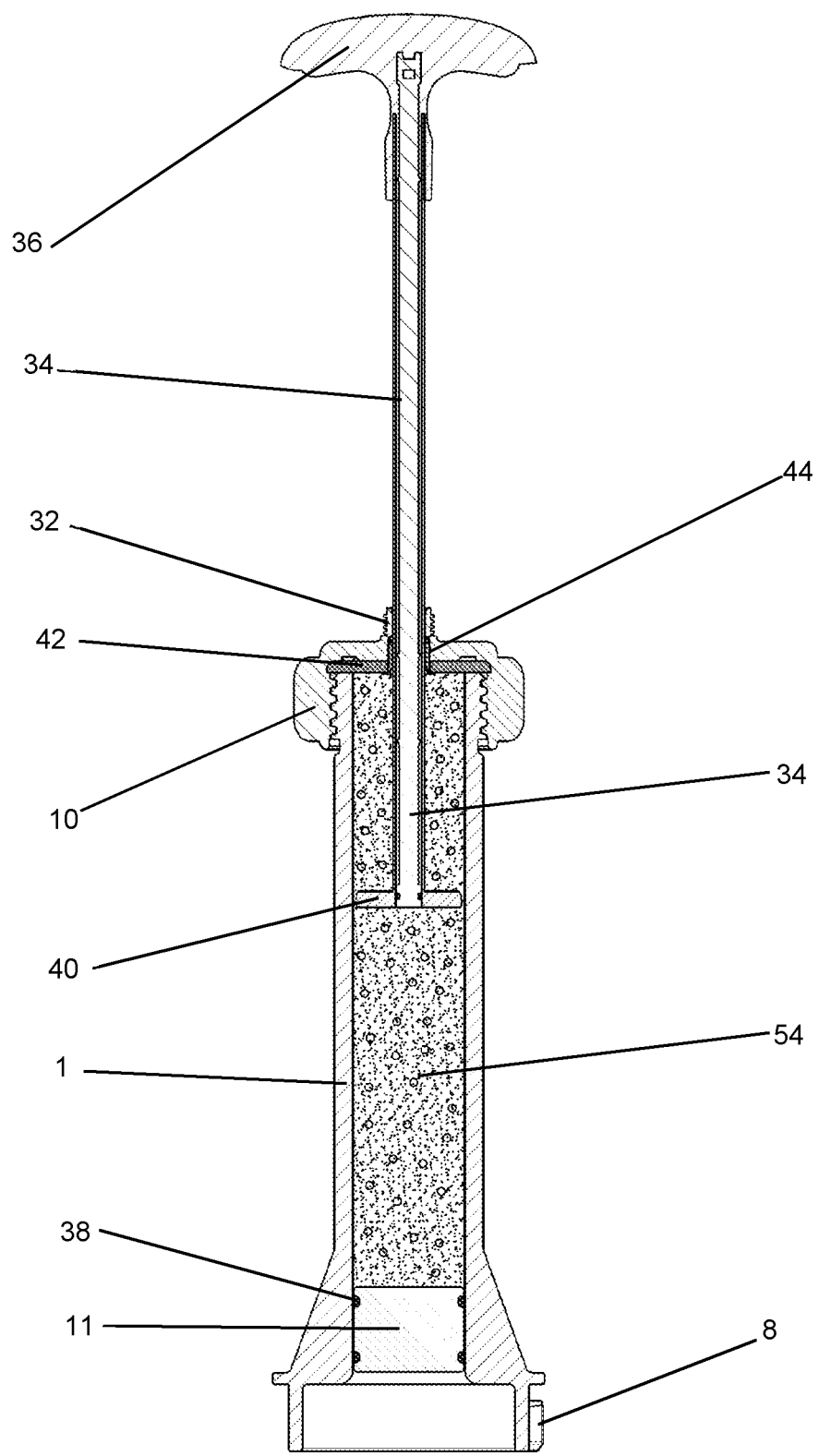
FIG. 14: shows a schematic cross-sectional view of the filled bone cement applicator according to FIG. 13, after the mixing process.

In the following, FIGS. 7 to 12 show the bone cement applicator in various states of assembly. FIGS. 7 and 8 show the bone cement applicator in the starting condition, FIGS. 9 and 10 show it with the three-way valve attached, and FIGS. 11 and 12 show it in a condition ready for application of the bone cement dough. FIGS. 13 to 17 show schematic cross-sectional views of the bone cement applicator according to the invention during an exemplary workflow of an application in chronological order and thus illustrate a method according to the invention.

In starting condition (FIGS. 7 and 8), a mixing rod 34 or a mixing tube 34 is guided through a socket 32, which has an external thread onto which the tube 3 is screwed in FIG. 1, and into the inside of the cartridge 1. The mixing rod 34 can be operated by means of a handle 36, i.e. it can be rotated with respect to the cartridge 1 and can be shifted in longitudinal direction of the cartridge 1.

Arranged on the rear side of the cartridge 1 (on the bottom in FIG. 8), the dispensing plunger 11 is sealed with respect to the internal wall of the cylindrical internal space of the cartridge 1 by means of two circumferential seals 38 made of rubber. The end of the mixing tube 34 that points inside the cartridge 1 has multiple mixing vanes 40 arranged on it, by means of which the content of the cartridge 1 can be mixed by hand. Accordingly, if the starting components 52 (see FIG. 13) have been filled into the cartridge, the mixing vanes 40 can be moved inside the cartridge 1 by pushing the mixing rod 34 in and out and by rotating it, and thus the starting components 52 are mixed with each other.

A pore disk 42 is clamped, and thus positioned, between the union nut 10 and the front edge of the cartridge walls 1. The pore disk 42 is impermeable for bone cement powder. A ring-shaped or ring disk-shaped free space is provided between the pore disk 42 and the union nut 10 and is implemented by means of a corresponding depression in the underside of the union nut 10. The vacuum connector 13 is connected to said free space. By this means, the internal space of the cartridge 1 can be evacuated through the vacuum connector 13 without cement powder from the inside of the cartridge 1 moving through the vacuum connector 13, since the cement powder is retained by the pore disk 42. By this means, the starting components 52 can be mixed with each other in a vacuum in order to obtain a bubble-free bone cement dough 54 (see FIG. 14). The mixing rod 34 is guided through a sealed guidance 44, in the form of a socket, through the union nut 10 such that neither the starting components 52 nor the bone cement dough 54 can leak in this place while the starting components 52 are being mixed.

Subsequently, the mixing rod 34 with the mixing vanes 40 is pulled out of the internal space of the cartridge 1. Then, the tube 3 with the three-way valve 2 and the hose 4 are screwed onto the socket 32 by means of a union nut 46 (see FIGS. 9 and 10). The three-way valve 2 is shown in the open position in this context. The three-way valve 2 is shown in FIG. 10 in the form of two longitudinal sectional views that extend perpendicular with respect to each other. Accordingly, the application opening 6 in Luer system adapter 5 is in fluid connection with the internal space of the cartridge 1.

Then, a trocar 48 with a cannula 50 is connected to the Luer system adapter 5. This extends the application opening 6 to the tip of the cannula 50. The application opening 6 on the tip of the trocar 48 is then in fluid connection, via the open three-way valve 2, with the internal space of the cartridge 1 (see FIGS. 12 and 15).

Figure 15:
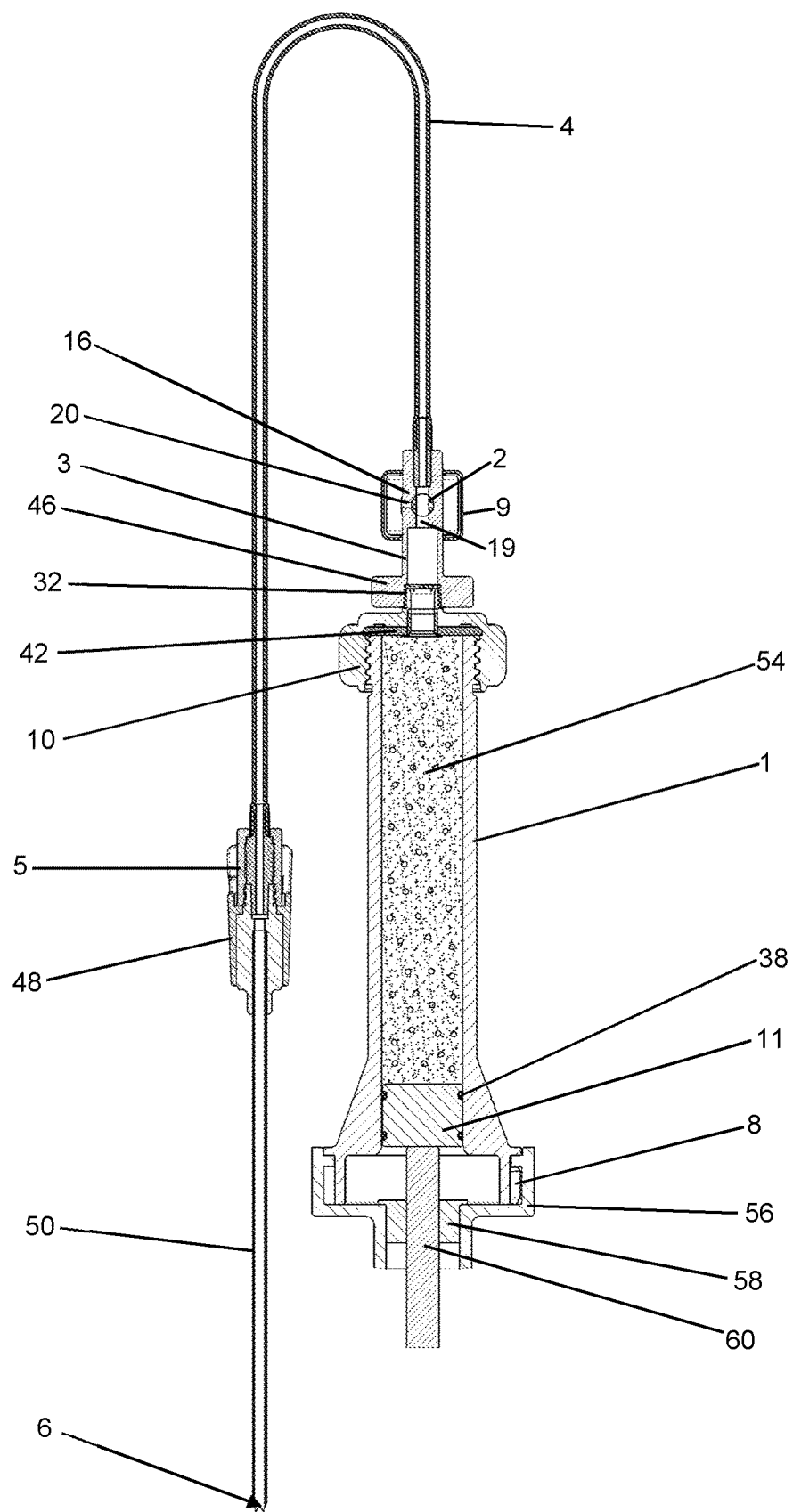
FIG. 15: shows a schematic cross-sectional view of the filled inventive bone cement applicator according to FIGS. 13 and 14, ready for application and inserted into an extrusion device.

The bone cement applicator can have been or can now be inserted into an extrusion device (see FIG. 15). Of the extrusion device, only a connector 56 that is connected to the connector 8 of the cartridge 1, a bearing 58, and a pestle 60 that is supported in the bearing 58 are shown in FIG. 15. The pestle 60 can be propelled by hand in longitudinal direction against the bearing 58. The pestle 60 touches against the rear side of the dispensing plunger 11, when the extrusion device is connected to the cartridge 1 and/or to the bone cement applicator.

Figure 16:
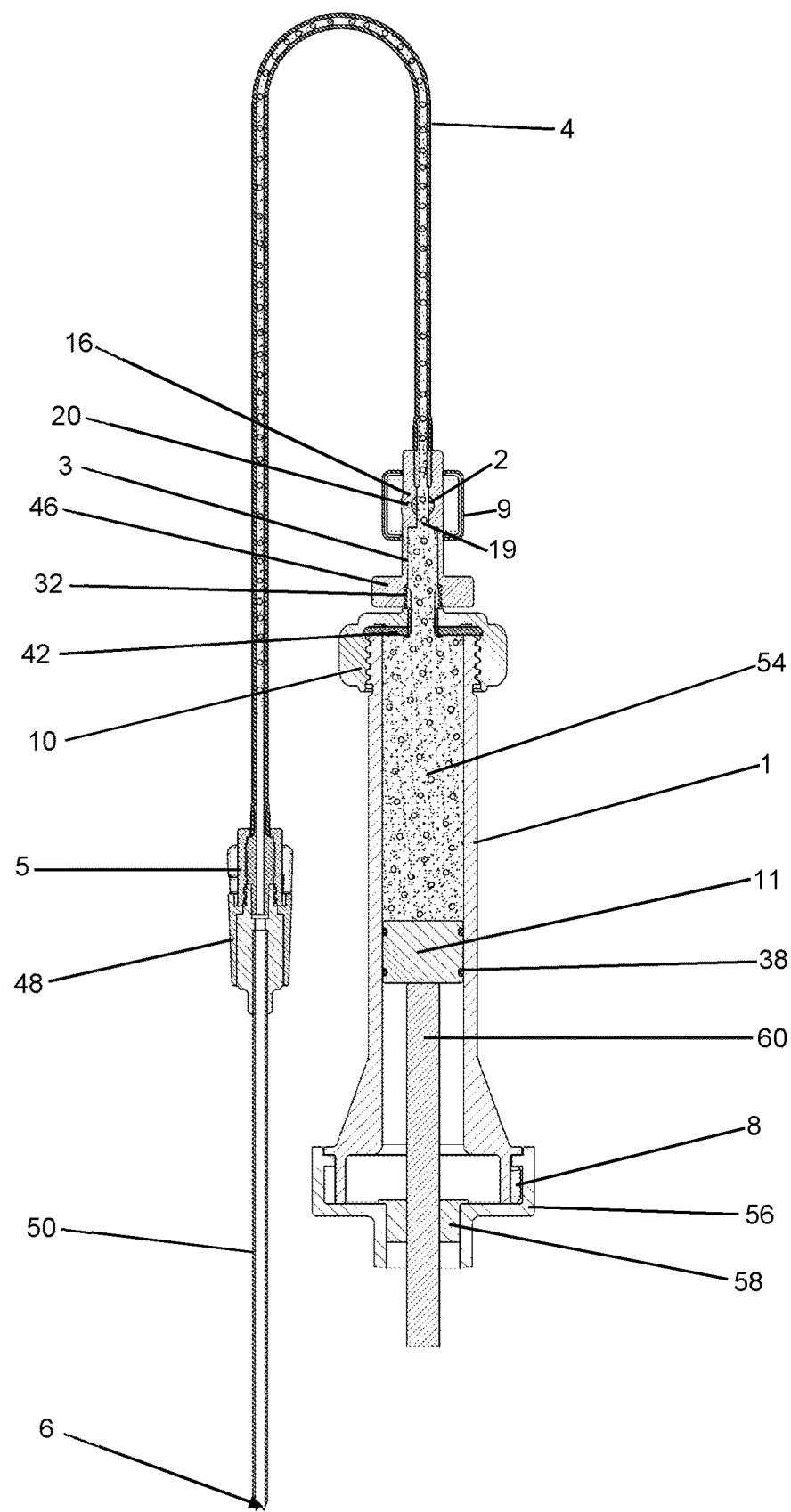
FIG. 16: shows a schematic cross-sectional view of the bone cement applicator according to FIGS. 13 to 15, during the extrusion of the bone cement dough.

Propelling the dispensing plunger 11 with the pestle 60 causes the bone cement dough 54 contained in the cartridge 1 to be pressed forward, through the tube 3 and through the open three-way valve 2 into the hose 4 (see FIG. 16). Propelling the dispensing plunger 11 forward even more causes the bone cement dough 54 to be driven through the trocar 48 such that it can be applied in or on the vertebra. In this context, the flow of the bone cement dough 54 can be interrupted at any time by closing the three-way valve 2, as is shown in FIG. 2, FIG. 3 top, and FIG. 4 bottom. The pressure that is built up in the hose 4 and in the trocar 48 and pressurises the bone cement dough 54 is partially released in this process such that the bone cement dough 48 flows through the three-way valve 2 via the feed-through 20 into the collecting container 9. By this means, the amount of the bone cement dough 54 that continues to flow through the application opening 6 is reduced substantially. Concurrently, the pressure is maintained between the three-way valve 2 and the dispensing plunger 11. By this means, the bone cement applicator is rapidly ready for use again, once the three-way valve 2 is opened again.

Figure 17:
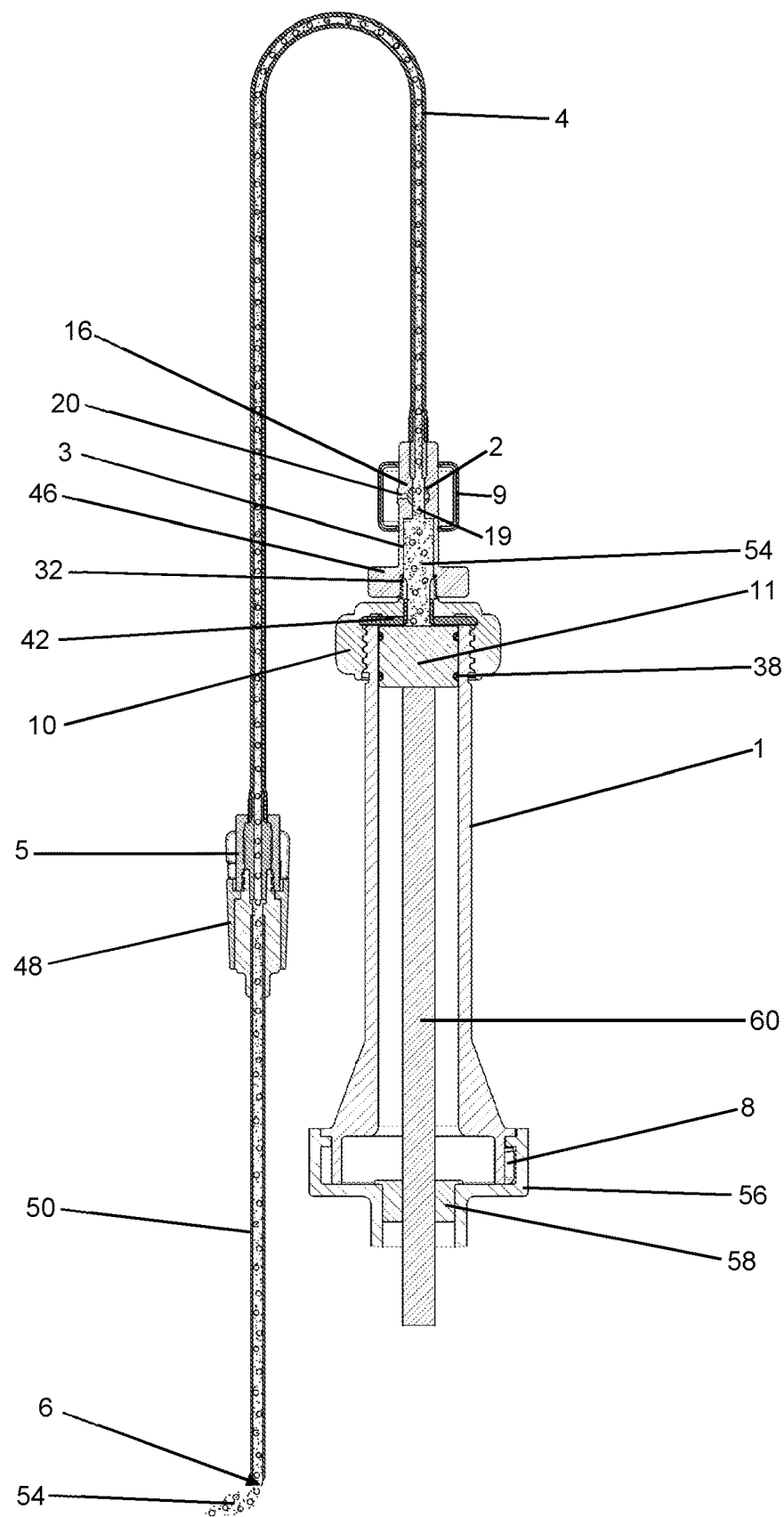
FIG. 17: shows a schematic cross-sectional view of the bone cement applicator according to FIGS. 13 to 16, after the extrusion of the bone cement dough.

Finally, the bone cement dough 54 is dispensed by extruding it completely from the cartridge 1 (see FIG. 17).

The features of the invention disclosed in the preceding description and in the claims, figures, and exemplary embodiments, can be essential for the implementation of the various embodiments of the invention both alone and in any combination.

LIST OF REFERENCE NUMBERS

1 Cartridge
2 Three-way valve
3 Tube
4 Hose
5 Luer system adapter
6 Application opening
7 T-handle
8 Connector
9 Collecting container
10 Union nut/cartridge head
11 Dispensing plunger
12 Sleeve
13 Vacuum connector
14 Static mixer
16 Valve seat
18 Insert
19 Passage
20 Feed-through
22 Stopper
24 External sleeve
26 Internal thread
28 Internal part
30 Cone
32 Socket with external thread
34 Mixing rod
36 Handle
38 Seal
40 Mixing vanes
42 Pore disk
44 Sealed guidance
46 Union nut
48 Trocar
50 Cannula
52 Starting components
54 Bone cement dough
56 Connector
58 Bearing
60 Pestle

The invention claimed is:

1. A bone cement applicator for application of a bone cement dough, the bone cement applicator comprising:
   a cartridge with an internal space;
   a dispensing plunger for expelling the starting components of the bone cement dough from the cartridge through an opening of the cartridge opposite from the dispensing plunger, wherein the dispensing plunger is mobile in longitudinal direction in the internal space of the cartridge;
   a hose;
   an application opening through which the bone cement dough is applicable;
   a three-way valve operable from outside and arranged in the hose or on a side of the hose facing the cartridge, wherein, when the three-way valve is connected to the cartridge, the three-way valve is in fluid connection with the opening of the cartridge, and the three-way valve is movable to at least a first position or a second position; and
   a collecting container arranged on the three-way valve for accommodation of bone cement dough,
   wherein the three-way valve is designed, arranged, or arrangeable in the bone cement applicator such that, when the three-way valve is in the first position, the three-way valve provides a fluid connection between the application opening and the opening of the cartridge and closes a feed-through to the collecting container and, when the three-way valve is in the second position, the three-way valve provides a fluid connection between the application opening and the collecting container and closes a passage to the opening of the cartridge.

2. The bone cement applicator according to claim 1, further comprising:
   a mixer for mixing of the bone cement dough arranged or arrangeable downstream from the opening of the cartridge or between the opening of the cartridge and the three-way valve or the hose, wherein the three-way valve is arranged or arrangeable between the mixer and the hose, wherein the three-way valve, being in the first position, provides a fluid connection between the application opening and the mixer and, being in the second position, closes the passage to the mixer.

3. The bone cement applicator according to claim 1, wherein the bone cement applicator is operable by means of a manually operated extrusion device and the dispensing plunger is movable in the cartridge by manual force, wherein the cross-section of the internal space of the cartridge is maximally 3.5 cm$^2$.

4. The bone cement applicator according to claim 1, wherein at least part of the hose is flexible and/or the application opening is arranged in a connection with an internal thread, in a Luer system adapter, or in a trocar.

5. The bone cement applicator according to claim 1, wherein the collecting container is fluid-tight or fluid-tight and gas-tight, and/or the collecting container has a volume that is at least as large as half the volume of the hose.

6. The bone cement applicator according to claim 1, wherein the cartridge comprises, on its rear side, an attachment element for attachment of an extrusion device.

7. The bone cement applicator according to claim 1, wherein the cartridge comprises a cylindrical internal space and/or the dispensing plunger closes off tightly against the internal wall of the cartridge by means of at least one circumferential seal and/or a wiper lip.

8. The bone cement applicator according to claim 1, wherein the opening of the cartridge is arranged in a cartridge head that is detachably connected to the cartridge, wherein an external thread is provided in the region of the opening by means of which the hose or the three-way valve is connected or connectable in pressure-tight manner by means of a sealing means.

9. The bone cement applicator according to claim 1, further comprising:
   a mixing facility provided by means of which the content of the cartridge is mixable in the internal space of the cartridge, wherein the mixing facility is operable from outside when the mixing facility is connected to the cartridge.

10. The bone cement applicator according to claim 9, wherein multiple mixing vanes, connected to a mixing rod, are arranged in the internal space of the cartridge, and are movable through axial linear motion and through rotation of the mixing rod, in the internal space of the cartridge to mix starting components in the internal space of the cartridge, when the mixing facility is connected to the cartridge.

11. The bone cement applicator according to claim 9, wherein a mixing rod of the mixing facility is guided through the opening of the cartridge into the internal space of the cartridge, wherein the mixing facility is drawable out of the cartridge, when the mixing facility is connected to the cartridge.

12. A method for application of a bone cement comprising:
   a) providing the bone cement applicator according to claim 1;
   b) filling a bone cement dough into the internal space of the cartridge or filling the starting components of the bone cement dough into the internal space of the cartridge;
   c) inserting the bone cement applicator into an extrusion device, wherein the extrusion device comprises an axially propellable pestle for propulsion of the dispensing plunger in the internal space of the cartridge in the direction of the opening of the cartridge;
   d) moving the three-way valve to the first position or the three-way valve being in the first position and extruding the content of the cartridge by means of the extrusion device by axial propulsion of a pestle of the extrusion device in the direction of the opening, wherein the pestle pushes the dispensing plunger in the direction of the opening, by means of which the bone cement dough is pushed through the hose and out of the application opening or wherein the starting components are mixed to form the bone cement dough and the bone cement dough is subsequently pushed through the hose and out of the application opening; and
   e) moving the three-way valve to the second position, wherein the three-way valve, in the second position of the three-way valve, stops the flow of the bone cement dough or of the starting components out of the cartridge into the hose and a part of the bone cement dough that is pressurized between the application opening and the three-way valve is pushed through the three-way valve into the collecting container.

13. The method according to claim 12, wherein the three-way valve is moved to the first position again in f) after e) and, by this means, the bone cement dough is guided again out of the cartridge through the three-way valve to the application opening, wherein d), e), and f) are repeatable once or multiple times in the order given.

14. The method according to claim 12, wherein, the starting components or the bone cement dough are filled into the internal space of the cartridge in b) and the starting components or the bone cement dough is pressed out of the cartridge in d).

15. The method according to claim 12, wherein, the starting components are filled into the internal space of the cartridge in b) and are mixed in the internal space of the cartridge with a mixing facility ahead of c), wherein the hose with the three-way valve is then attached to the cartridge, wherein the mixing facility is removed from the cartridge before the hose with the three-way valve is connected.

* * * * *